(12) United States Patent
Dietzschold et al.

(10) Patent No.: US 7,074,413 B2
(45) Date of Patent: Jul. 11, 2006

(54) GENETICALLY ENGINEERED RABIES RECOMBINANT VACCINE FOR IMMUNIZATION OF STRAY DOGS AND WILDLIFE

(75) Inventors: Bernhard Dietzschold, Newtown Square, PA (US); D. Craig Hooper, Medford, NJ (US); Matthias Schnell, Harleysville, PA (US); Charles E. Rupprecht, Lawrenceville, GA (US)

(73) Assignee: Thomas Jefferson University, Philadelphia, PA (US)

( * ) Notice: Subject to any disclaimer, the term of this patent is extended or adjusted under 35 U.S.C. 154(b) by 370 days.

(21) Appl. No.: 09/816,531

(22) Filed: Mar. 23, 2001

(65) Prior Publication Data

US 2002/0131981 A1 Sep. 19, 2002

Related U.S. Application Data

(60) Provisional application No. 60/191,510, filed on Mar. 23, 2000.

(51) Int. Cl.
*A61K 39/12* (2006.01)

(52) U.S. Cl. .............................. 424/199.1; 424/224.1; 435/235.1; 435/236

(58) Field of Classification Search .............. 424/224.1, 424/199.1; 435/235.1, 236
See application file for complete search history.

(56) References Cited

U.S. PATENT DOCUMENTS 5,853,735 A   12/1998   Benejean et al. ......... 424/208.1

FOREIGN PATENT DOCUMENTS

WO    WO 01/70932    9/2001

OTHER PUBLICATIONS

Morimoto et al., Journal of Neurovirology, vol. 6, No. 5, pp. 373–381, Oct. 2000.*
Allen and Seed (1989) *Science* 243:378–80.
Berg et al. (1995) *J. Clin. Invest.* 96:2339–2347.
Bogdan et al (1991) *J. Exp. Med.* 174:1549–1555.
Carrera et al. (1996) *J. Exp. Med.* 183:515–526.
Cassatella et al. (1989) *J. Exp. Med.* 169:549–567.
Chattergoon et al. (2000) *Nat. Biotech.* 18:974–979.
Chehimi et al. (1994) *J. Exp. Med.* 179:1361–1366.
Cohn et al. (1946) *J. Am. Chem. Soc.* 68:459–475.
Conzelman (1998) *Ann. Rev. Genet.* 32: 123–162.
Dalrymple et al. (1995) *Infect. Immun.* 63:2262–2268.
D'Andrea et al. (1993) *J. Exp. Med.* 178:1041–1048.
Davidson et al. (1996) *J. Exp. Med.* 184:241–251.
Dietzchold et al. (1983) *Proc. Natl. Acad. Sci. USA* 80:70–74.
Dietzschold et al. (1985) *J. Virol.* 56:12–18.
Dietzchold et al. (1999) *Molecular Pathogenesis of Rabies*, Abstract Presentation, 10th Annual Rabies in Americas, Nov. 14–19, San Diego, CA.
Dietzschold et al. (2000) *J. Human Virol.* 3:50–57.
Faber et al. (2002) *J. Virol.* 76:3374–3381.
Finke et al. (2000) *J Virol.* 74:7261–7269.
Fiorentino et al. (1991) *J. Immunol.* 146:3444–3451.
Galelli et al. (2000) *J. Neurovirol.* 6: 359–372.
Gavin et al. (1998) *J. Immunol.* 160:20–23.
Germann et al. (1995) *Proc. Natl. Acad. Sci. USA* 92:4823–4827.
Hale et al. (1988) *Lancet* 2: 1394–1399.
Hart et al. (1995) *Immunol.* 84:536–542.
Hazenbos et al. (1996) *Immunity* 5:181–188.
Heinzel et al. (1993) *J. Exp. Med.* 177:1505–1512.
Howard et al. (1993) *J. Exp. Med.* 177:1205–1208.
Jallet et al. (1999) *J. Virol.* 73:225–233.
Jones et al. (1986) *Nature* 321:522–525.
Karp et al. (1996) *Science* 273:228–231.
Kincy–Cain et al. (1996) *Infect. Immun.* 64:1437–1440.
Kleinveld et al. (1988) *Scand. J. Rheumatology* 75:157–163.
Kothakota et al. (1997) *Science* 278:294–297.
Kunkel et al. (1988) *J. Biol. Chem.* 263:5380–5384.
Lee et al. (1988) *J. Chromatography* 444:141–52.
Leonard et al. (1995) *J. Exp. Med.* 181:381–386.
Malefyt et al. (1991) *J. Exp. Med.* 174:1209–1220.
Malefyt et al. (1991) *J. Exp. Med.* 174:915–924.
Mattner et al. (1996) *Eur. J. Immunol.* 26:1553–1559.
Mebatsion et al. (1995) *J. Virol.* 69(3):1444–1451.
Mebatsion et al. (1996) *Proc. Natl. Acad. Sci. USA* 93(21):11366–11370.
Morimoto et al. (1996) *Proc. Natl. Acad. Sci. USA* 93:5653–5658.
Morimoto et al. (1999) *J. Virol.* 73: 510–517.
Morimoto et al. (2000) *J. Neurovirol.* 6:373–381.
Morimoto et al. (2001) *Vaccine* 19:3543–3551.
Muta et al. (1994) *Nature* 368:70–73.
Nathan (1987) *J. Clin. Invest.* 79:319–326.

(Continued)

Primary Examiner—James Housel
Assistant Examiner—Myron G. Hill
(74) *Attorney, Agent, or Firm*—Raymond A. Miller; John E. Pillion; Pepper Hamilton LLP

(57) ABSTRACT

Live, attenuated recombinant rabies virus vaccines are generated using reverse genetics to combine the antigenic determinants that render the rabies virus non-pathogenic with the determinants that are responsible for the elicitation of an effective anti-rabies immune response. These vaccines do not affect the antigenic, and therefore the immunogenic, properties of the virus. The present invention further relates to recombinant rabies virus vaccines that express a pro-apoptotic protein, such as cytochrome c, to increase the capacity to induce apoptosis, thereby enhancing the protective immunity against rabies. This new generation of live rabies virus vaccines represents a safe and effective approach to the eradication of rabies in wildlife, and subsequently humans and livestock.

16 Claims, 12 Drawing Sheets

OTHER PUBLICATIONS

Noel et al. (1992) *J. Infec. Dis.* 166:178–182.
Oncley et al. (1949) *J. Am. Chem. Soc.* 71:541–550.
Pulmanausahakul et al. (2001) *J. Virol.* 75(22): 10800–10807.
Queen et al. (1989) *Proc. Natl. Acad. Sci. USA* 86:10029–10033.
Reid et al. (1997) *J. Immunol.* 159:970–975.
Reiner et al. (1993) *J. Immunol. Methods* 165:37–46.
Restifo (2000) *Curr. Opin. Immunol.* 12: 597–603
Rovere et al. (1998) *J. Immunol.* 161: 4467–4471.
Sasaki et al. (2001) *Nat. Biotech.* 19: 543–547.
Schnell et al. (1999) *Recombinant Rabies Virus as Potential Live–Viral Vaccines for HIV–1*, Abstract Presentation, 10th Annual Rabies in the Americas, Nov. 14–19, San Diego, CA.
Sears et al. (1990) *J. Immunol.* 144:371–78.
Shi et al. (2000) *Proc. Natl. Acad. Sci. USA* 97: 14590–14595.
Sutterwala et al. (1997) *J. Exp. Med.* 185:1977–1985.
Sutterwala et al. (1996) *J. Leukocyte Biol.* 59:883–890.
Takai et al. (1994) *Cell* 76:519–529.
Takai et al. (1996) *Nature* 379:346–349.
Tankersley (1994) *Immunol. Reviews* 139:159–172.
Trembleau et al. (1995) *J. Exp. Med.* 181:817–821.
Trinchieri et al.(1996) *J. Leukocyte Biol.* 59:505–511.
Tripp et al. (1993) *Proc. Natl. Acad. Sci. USA* 90:3725–3729.
Tsunawaki et al. (1988) *Nature* 334:260–262.
Verhoeyen et al. (1988) *Science* 239:1534–1536.
Vialtel et al. (1982) *J. Biol. Chem.* 257:3811–3818.
Virag et al. (1998) *Immunol.* 94: 345–355.
Wiktor (1977) *Proc. Natl. Acad. Sci. USA* 74:334–338.
Wright et al. (1980) *Biochem J.* 187:767–774.
Wysocka et al. (1995) *Eur. J. Immunol.* 25:672–676.
Yan et al. (2001) *J. Neurovirol.* 7: 518–527.

* cited by examiner

Fig. 2

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: primers

<400> SEQUENCE: 1
aaacgtacga atatgggtga tgttgagaa                                      29

<210> SEQ ID NO 2
<211> LENGTH: 33
<212> TYPE: DNA
<213> ORGANISM: Artificial Sequence
<220> FEATURE:
<223> OTHER INFORMATION: primers

<400> SEQUENCE: 2
gaagctagct tactcattag tagctttttt gag                                 33

<210> SEQ ID NO 3
<211> LENGTH: 24
<212> TYPE: DNA
<213> ORGANISM: Artificial Sequence
<220> FEATURE:
<223> OTHER INFORMATION: primers

<400> SEQUENCE: 3
gtggcactgg gatcacttca taat                                           24

<210> SEQ ID NO 4
<211> LENGTH: 24
<212> TYPE: DNA
<213> ORGANISM: Artificial Sequence
```

```
                                -continued

<220> FEATURE:
<223> OTHER INFORMATION: primers

<400> SEQUENCE: 4
attatgaagt gatcccagtg ccac                                            24
```

GENETICALLY ENGINEERED RABIES RECOMBINANT VACCINE FOR IMMUNIZATION OF STRAY DOGS AND WILDLIFE

CROSS REFERENCE TO RELATED APPLICATIONS

This application claims priority in part under 35 U.S.C. §119 based upon U.S. Provisional Patent Application No. 60/191,510 filed Mar. 23, 2000.

GOVERNMENT RIGHTS IN THE INVENTION

This invention was made in part with government support under Grant numbers AI45097, 5RO1A145097-02, and AI41544 awarded by the National Institutes of Health. The government has certain rights to the invention.

FIELD OF INVENTION

The present invention relates to the field of biotechnology and immunology, and more particularly to the design of recombinant rabies virus vaccines by replacing the glycoprotein of a non-neuroinvasive rabies strain with that of a street rabies virus and/or by constructing a recombinant rabies virus expressing a pro-apoptotic protein, thereby eliciting an optimal immunoprotective response against rabies virus.

BACKGROUND OF THE INVENTION

The rabies virus is a rhabdovirus, a nonsegmented RNA virus with negative sense polarity. The genome codes for five proteins: 3 internal proteins are an RNA-dependent RNA polymerase (L), a nucleoprotein (N) and a phosphorylated protein (NS); a matrix protein (M) located on the inner side of the viral envelope and an external surface glycoprotein (G). (Dietzschold, B. & Ertl, H. *Cricial Rev. in Immunology* 10:427–439, 1991). The virus is transmitted through broken skin by the bite or scratch of an infected animal. This exposure to rabies virus results in its penetration of peripheral unmyelineated nerve endings, followed by spreading through retrograde axonal transport, replication occurring exclusively in the neurons, and finally arrival in the central nervous system (CNS). Infection of the CNS causes cellular dysfunction and ultimately death. (Rupprecht, C. E., & Dietzschold, B. *Lab Invest.* 57:603, 1987). Since rabies virus spreads directly from cell to cell, it evades immune recognition. (Clark, H. F. & Prabhakar, B. S., Rabies, In: Olson R. G., et al., eds., *Comparative Pathology of Viral Disease*, 2:165, Boca Raton, Fla.: CRC Press, 1985). Therefore, in order to effectively prevent disease, immunization should inhibit the ability of the virus to enter the cells.

Rabies is a worldwide public health problem. There is no successful treatment of clinical rabies, the outcome is almost always fatal. The rabies virus is maintained in many animal reservoirs, wildlife as well as domestic. Therefore, in order to eliminate pathogenesis in humans, as well as livestock, it is necessary to eliminate these viral reservoirs. The most efficient vaccination protocol would be the development of oral vaccines that induce a long-lasting protection against subsequent exposure to the rabies virus. It has been shown that certain rabies virus variants, such as SAG-2 and SAD B19, or a vaccinia rabies virus glycoprotein recombinant virus are effective vaccines that can be used for the oral vaccination of certain wildlife, such as foxes and raccoons. (Rupprecht, C. E., et al., *Emerg. Infect. Dis.*, 1:107–114, 1995). However, these vaccines do not induce sufficient protective immunity when administered orally to dogs, and it is the domestic dog that is the principal host and major vector of rabies throughout the world. (Fekadu, M., Canine Rabies, In: Baer, G. M., ed. *The Natural History of Rabies*, 367–378, Boca Raton, Fla.: CRC Press, 1991; Wang, Y. & Walker, P. J., *Virology* 195:719–731, 1993).

In developing countries, dogs are responsible for ~94% of human rabies deaths. For example, in Thailand, which has an estimated population of 7 million dogs, one of every 961 dogs was found to test positive for rabies. Assuming a mean vaccination cost of one U.S. dollar per dog, the minimum spending for dog vaccination in developing countries would be around U.S. $50,000,000. (Meslin, F. X., et al., In: *Lyssaviruses*, Rupprecht, C. E., et al., eds., Springer-Verlang, Berlin, Heidelberg, New York, 1–26, 1994).

In the Americas, the rabies situation is much more complex than that of developing countries. Reservoirs of rabies exist in many diverse wild animal species, in the United States these resevoirs accounted for nearly 93% of the 8513 reported cases of rabies in 1997. (Rupprecht, C. E., et al., *Emerging Infectious Diseases* 1(4): 107–114, 1995). The most frequently reported rabid wildlife species are raccoons (50.5%), followed by skunks (24.0%). (Rupprecht, C. E., et al., *Emerging Infectious Diseases* 1(4): 107–114, 1995). Outbreaks of rabies infections in these terrestrial mammals are found in broad geographic areas across the United States. For example, raccoon rabies affects an area of more than 1 million square kilometers from Florida to Maine.

Oral immunization of stray dogs and wildlife against rabies is the most effective method to control, and eventually eradicate, rabies. (Winkler, W. G. & Bogel., K. *Sci. Amer.*, 266(6):86–92, 1992). In this regard, significant progress has been made in the development of oral rabies vaccines for the control of vulpine rabies. (Aubert, M. F. A., et al., *Lyssaviruses*, Rupprecht, C. E., et al., eds., Springer-Verlang, Berlin, Heidelberg, New York, 219–243, 1994). However, while oral immunization with conventional modified-live vaccines such as SAD B19, SAG-2, or poxvirus-rabies glycoprotein recombinant vaccines are very effective in foxes (Aubert, M. F. A., et al., *Lyssaviruses*, Rupprecht, C. E., et al., eds., Springer-Verlang, Berlin, Heidelberg, New York, 219–243, 1994), they do not immunize skunks or induce only low seroconversion by the oral route (Rupprecht, C. E., et al., *J. Wildl. Dis.* 99–102, 1990). Moreover, very high doses of these vaccines ($>10^{8.5}$ $TCID_{50}$) are necessary to induce protective immunity via oral immunization of dogs. (WHO Report of the 4$^{th}$ WHO consultation on oral immunization of dogs against rabies, Geneva, *RabRes*, 93:42, 1993). These findings make oral field vaccinations economically impractical. Therefore, in order to control wildlife rabies and rabies in stray dogs worldwide, more potent and cost effective oral rabies vaccines must be developed. There is a high demand for such vaccines. For example, based on previous experience that a minimal density of 20 vaccine-laden baits per square mile is sufficient for immunization of foxes (Aubert, M. F. A., et al., *Lyssaviruses*, Rupprecht, C. E., et al., eds., Springer-Verlang, Berlin, Heidelberg, New York, 219–243, 1994), more than 20 million doses of vaccine alone would be required for the control of the raccoon rabies enzootic in the Atlantic regions of the United States.

Vaccines prepared with antigenically conserved lab rabies virus strains may not be effective against those found in the wild, i.e., the street virus. There is a need for versatile vaccines suitable for both domestic animals and wildlife, which either serve as reservoirs for human rabies or are economically important species. Efforts have been made to protect free-ranging animals against virulent street virus challenge by oral consumption of a potent vaccine contained within an attractive bait. Yet concerns regarding residual virulence and ineffectiveness remain. Therefore, there exists a long felt need for a new generation of live rabies vaccines. The present invention describes a new generation of live rabies vaccines that has been developed using reverse genetics technology. (Schnell, M. J., et al., *EMBO* 13:4195–4203, 1994).

In addition to virus-neutralizing antibodies (VNA), which are believed to be the major immune effectors against rabies, rabies virus antigen-specific (CD4$^+$) T helper cells and cytotoxic T cells (CD8$^+$) (Cox, J. H., et al., *Infect. Immun.* 16:754–759, 1977), as well as innate mechanisms (Hooper, D. C., et al., *J. Virol.* 72:3711–3719, 1998), play an important role in the immune defense against rabies. The rabies virus glycoprotein (G) induces the production of VNA, while the cellular responses of CD4$^+$ and CD8$^+$ T cells are predominantly triggered by the internal rabies virus proteins; therefore, live rabies virus represents the best immunogen that will confer optimal protective immunity.

The extent of the immune response to immunization with a live virus vaccine is determined by the antigenic mass administered and produced after administration of the vaccine. Inoculation with a live, yet attenuated, virus will allow for the production of antigen in the absence of pathogenicity. The site of antigen production and presentation are also important factors that determine the potency of the vaccine. In this context, the fixed and street rabies virus variants differ substantially in their ability to replicate in neuronal versus non-neuronal cells (neuronal specificity index). (Morimoto, K., et al., *J. Neuro Virol.*, 6:373–381, 2000). The neuronal specificity index of any particular rabies virus variant is determined by its glycoprotein. The glycoprotein is also the major viral protein that determines the host specificity of the strain. In this context, it is the rabies glycoprotein that carries the major determinants responsible for the pathogencity of the virus, as well as the determinants that trigger a protective immune response. One aspect of the present invention uses reverse genetics to combine the determinants that render the rabies virus non-pathogenic with the antigenic determinants that are responsible for the elicitation of an effective anti-rabies immune response.

Tissue culture-adapted laboratory and street rabies virus strains differ greatly in their ability to cause a lethal rabies virus encephalitis. (Morimoto, K., et al., *J. Neuro Vrol.* 6:373–381, 2000). The pathogenicity of individual rabies virus strains for immunocompetent adult mice appears to correlate inversely with their capacity to induce cell death in vitro and in vivo. For example, CVS-N2c, a highly pathogenic variant derived from the mouse-adapted CVS-24 rabies virus strain, was recently shown to induce significantly less apoptosis in primary hippocampal neuron cultures than the less pathogenic variant CVS-B2c. (Morimoto, K., et al., *J. Virol.* 73:510–517, 1999). The extent of apoptosis seen in neurons infected with the different viruses was associated with their levels of rabies virus G protein expression. CVS-B2c infection caused the expression of high levels of G protein and extensive apoptosis while CVS-N2c induced only minimal G protein production and limited apoptosis. The correlation of pathogenicity with cell death led to the speculatulation that the pathogenicity of a particular rabies virus may be dependent upon the capacity to avoid inducing a strong antiviral immune response. (Morimoto, K., et al., *J. Virol.* 73:510–517, 1999).

Unlike highly pathogenic rabies viruses, which fail to elicit a protective immune response, infection with weakly pathogenic tissue culture-adapted rabies viruses induces a strong antiviral response. In particular, rabies virus-specific cytotoxic T cells (Wiktor, T. J., et al., *Proc. Natl. Acad. Sci.* 74:334–338, 1977; Wiktor, T. J., et al., *J. Ex. Med.* 145:1617–1622, 1977) as well as G protein-specific VNA (Wandeler, A. I., et al., *Rev Infect. Dis.* 10 suppl. 4:649–653, 1988), which are considered to be the major effectors in the immune defense against a lethal rabies virus infection. (Cox, J. H., et al., *Infect. Immun.* 16:754–759, 1977). Therefore, virus-induced cell death may make an important contribution to the stimulation of the rabies virus-specific immune response. In this context, it has been suggested that virus-induced apoptosis may have a physiological role in protecting the CNS from progression of infection and allowing contact between virus and immune components. (Galelli, A., et al., *J. Neuro Virol.* 6:359–372, 2000). Thus, the enhanced immunogenicity of attenuated rabies virus strains could be associated with increased cell death.

While apoptosis occurring under certain physiological conditions, such as during development, is an immunologically innocuous event, apoptotic death after viral infection or ligation of Fas can trigger powerful innate and adaptive immune responses. (Restifo, N. P., *Current Opinion in Immunol.* 12:597–603, 2000). The possibility that cells undergoing apoptosis induce signals that enhance the immune response to the virus is supported by findings demonstrating that cell injury releases endogenous adjuvants that stimulate cytotoxic T cell responses. (Shi, Y., et al., *Proc. Natl. Acad. Sci.* 97:14590–14595, 2000). Furthermore, apoptotic cells can induce maturation of dendritic cells and stimulate their presentation of antigen to both class I- and class II-restricted T cells. (Chattergoon, M. A., et al., *Nature Biotechnology* 18:974–979, 2000; Rovere, P., et al., *J. Immunol.* 161:4467–4471, 1998). The present invention relates to the ability of less pathogenic rabies viruses to cause an increase in cell death, thereby inducing an immunogenic response against the rabies virus.

The invention disclosed herein relates to the construction of a recombinant rabies virus expression vector that expresses a pro-apoptotic protein, for example cytochrome c, thereby stimulating antiviral immunity against the rabies virus. (Schnell, M. J. et al., *Proc. Natl. Acad. Sci. USA* 97:3544–3549, 2000; Schnell, M. J. et al., *EMBO J.* 13:4195–4203, 1994) cytochrome c is essential for the proteolytic activity of Apaf-1 and the activation of caspases (Harvey, N. L. & Kumar, S., *Adv. Biochem. Engineering-Biotechnol.* 62:107–128, 1998) and causes an acceleration of apoptotic cell death if overexpressed. (Bradham, C. A., et al., *Mol. Cell. Biol.* 18:6353–6364, 1998). The modular genome organization of the rabies virus readily allows genetic manipulations of viral genes and stable expression of large foreign genes up to 4 kb. (Schnell, M. J., et al., *Proc. Natl. Acad. Sci. USA* 97:3544–3549, 2000). Cytochrome c is used herein as an example of a pro-apoptotic protein, but it is obvious to those of skill in the art that variations in the pro-apoptotic protein may be used, and it is intended that the invention may be practiced otherwise then as specifically described herein. Examples of pro-apoptotic proteins that are also used in the present invention include, but are not limited to, Bad, caspase, Bok, Bax, Bak, Fas, etc. Cytochrome c plays a role in the induction of nuclear apoptosis and is highly conserved between species such that any effect on the immunogenicity of a rabies virus vaccine strain in mice will be applicable to other target species. The expression of cytochrome c by a rabies recombinant virus of the present invention will accelerate cell death, enhance immunogenicity, and attenuate pathogenicity of the rabies virus.

SUMMARY OF THE INVENTION

It is an object of the present invention to provide a rabies virus vaccine wherein a non-neuroinvasive glycoprotein gene of a non-neuroinvasive rabies virus is replaced with a glycoprotein gene of a neuroinvasive rabies virus to produce an attenuated recombinant rabies virus for vaccination. In one embodiment the rabies virus vaccine is delivered by an oral vaccination. In one embodiment the attenuated recombinant rabies virus of the vaccine slows down the uptake of a rabies virus into a cell. In one embodiment the cell is a neuron. In a further embodiment the glycoprotein gene of the neuroinvasive rabies virus is a glycoprotein gene encoding a cytoplasmic tail from a heterologous glycoprotein gene. In yet another embodiment the glycoprotein gene of a neuroinvasive rabies virus has a change in an amino acid.

It is a further object of the present invention to provide a rabies virus vaccine wherein a pro-apoptotic gene is inserted into the rabies virus such that a pro-apoptotic protein is expressed from the pro-apoptotic gene to produce a recombinant rabies virus for vaccination. In one embodiment the pro-apoptotic gene is a cytochrome c gene. In one embodiment the vaccination is an oral vaccination. In one embodiment the pro-apoptotic protein induces an acceleration of apoptosis. The acceleration of apoptosis can enhance an immune response against the rabies virus. In one embodiment the recombinant rabies virus vaccine attenuates the pathogenicity of a rabies virus.

It is a further object of the present invention to provide a rabies virus vaccine wherein a pro-apoptotic gene is inserted into the rabies virus such that a pro-apoptotic protein is expressed from the pro-apoptotic gene and further wherein a glycoprotein gene of the rabies virus is replaced with a glycoprotein gene of a neuroinvasive rabies virus to produce an attenuated recombinant rabies virus for vaccination. In one embodiment the pro-apoptotic gene is a cytochrome c gene. In another embodiment the vaccination is an oral vaccination. In a further embodiment of the vaccine the glycoprotein gene of the neuroinvasive rabies virus is a glycoprotein gene encoding a cytoplasmic tail from a heterologous glycoprotein gene. In another embodiment of the vaccine the glycoprotein gene of the neuroinvasive rabies virus has a change in an amino acid. In yet another embodiment the pro-apoptotic protein induces an acceleration of apoptosis. In yet a further embodiment of the vaccine the acceleration of apoptosis enhances an immune response against the rabies virus.

BRIEF DESCRIPTION OF THE DRAWINGS

FIG. 2. Pathogenicity indices of rabies virus recombinants and the corresponding parental viruses.

DESCRIPTION OF THE INVENTION

Materials and Methods

Viruses.

CVS-N2c is a hghly pathogenic and CVS-B2c a less patogenic subclone of the mouse-adapted CVS-24 rabies virus. (Morimoto, K., et al., *Proc. Natl. Sci USA* 95:3152–3156, 1998). The recombinant rabies viruses SPBN, SN-10, and SN10-333 are generated from a SAD B19 cDNA clone as described elsewhere. (Schnell, M. J., et al., *Proc. Natl. Acad. Sci. USA* 97:3544–3549, 2000; Schnell, M. J., et al., *EMBO J.* 13:4195–4203, 1994; Morimoto, K., et al., *Vaccine* in press, 2001).

Development of Recombinant Virus Vaccines for the Oral Immunization of Dogs, Raccoons, and Skunks Preliminary data obtained from mouse protection experiments demonstrated great variations in the protective activity of recombinant rabies virus vaccines against infection with particular rabies challenge viruses. Since the potency of a recombinant vaccine can increase as much as 16-fold if the antigenic structures of the G proteins of the vaccine virus and the challenge virus are identical, an object of the present invention is the construction of recombinant viruses expressing the G proteins of street rabies viruses associated with dogs, raccoons, or skunks. These recombinant vaccines will incorporate the cDNA clones of the G proteins of a Mexican dog rabies virus (DRV-4), a raccoon rabies virus from the Mid-Atlantic region of the USA (RRV-27), and a skunk rabies virus from the Central region of the USA (SRV-16).

Figure 1:
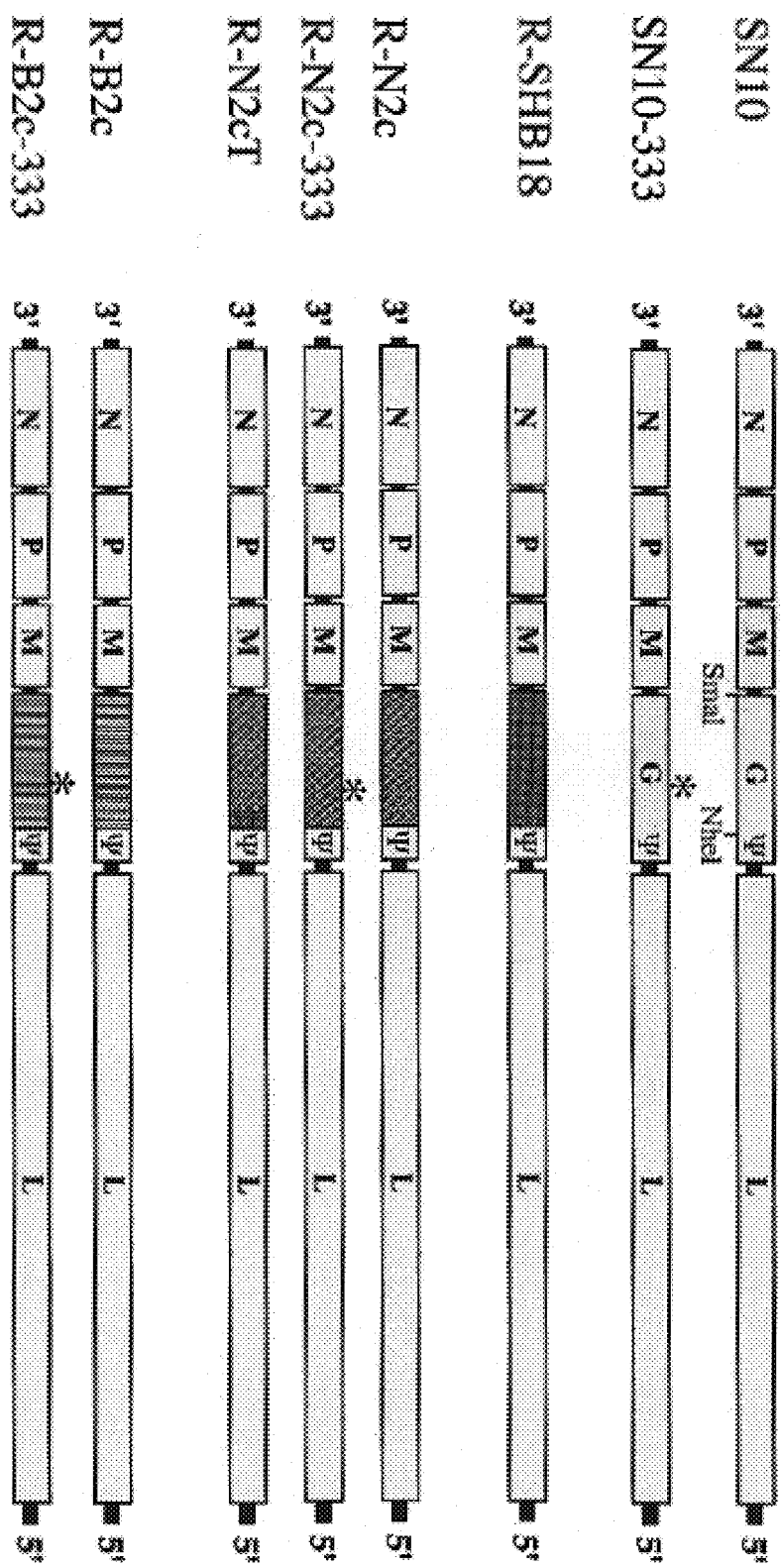
FIG. 1. Diagram showing the design of rabies virus recombinant vaccines. Using reverse genetics the G protein gene of the SN-10 strain was removed and replaced by the G protein genes of the SHBRV-18, CVS-N2c, or CVS-B2c strain resulting in the recombinant viruses R-SHB18, R-N2c, and R-B2c. R-N2cT was obtained by replacing the cytoplasmic tail of its G protein with the cytoplasmic tail of the SHBRV-18 G-protein. * Indicates the introduction of an arg→gln mutation at position 333 of the G protein.

To obtain recombinant viruses, a Sma I restriction enzyme site is added to the 5' end and an Nhe I restriction enzyme site is added to the 3' end of the G protein cDNA clones by site-directed mutagenesis. The G protein gene of the full length SN10 cDNA clone (see FIG. 1) is excised using Sma I and Nhe I restriction enzymes and replaced by the modified dog, raccoon, or skunk rabies virus G cDNA clones and ligated into the SN10 vector. Infectious viruses are recovered after transfection of the recombinant cDNA clones into BSR cells as previously described. (Schnell, M. J., et al., *EMBO J.*, 13:4195–4203, 1994). If necessary, a glutamine$^{1055}$→arginine$^{1055}$ mutation will be introduced by site-directed mutagenesis within the G protein gene. This mutation replaces the arginine at position 333 of the G protein with glutamine, thereby generating R-DRV-333, R-RRV-333 and R-SRV-333. This change in the G protein results in a complete loss of viral pathogenesis. (Dietzschold, B., et al., *Proc. Natl. Acad. Sci., USA*, 80:70–74, 1982). Alternately, to achieve further attenuation, the cytoplasmic tail of the G proteins of the recombinant viruses are exchanged with the cytoplasmic tail sequence of the SHBRV-18 G protein, thereby generating R-DRVT, R-RRVT and R-SRVT.

Following virus recovery from cDNA clones, virus stocks are prepared by injecting the rescued viruses intracranially (i.c.) into newborn mice, because suckling mouse brain is the best tissue known to support rabies virus replication. Three days after infection, brains are removed and used to prepare a 20% suspension in PBS. The virus stocks are used to produce vaccine batches. The vaccine batches are prepared by infecting monolayers of BSR (subclone of BHK-21 cells) with the individual stock viruses at a multiplicity of infection (m.o.i.) of 0.1. The virus is harvested at 3 days after infection. The infected cells are replenished with culture medium, incubated for another 3 days and then tissue culture supernatant is harvested again ($2^{nd}$ harvest). The virus titer of the individual virus harvests is determined by infection of mouse neuroblastoma cells with serial 10-fold dilutions of the virus batches, followed by detection of infected cells with the direct immunofluorescence antibody technique. The vaccine batches are aliquoted and stored at −80° C. To ascertain that no mutation had occurred in the G protein genes during the genetic manipulations and virus culturing, aliquots of the vaccine batches are subjected to DNA sequence analysis and the G protein gene sequences of viruses are compared with those of the parental viruses. For each vaccine, a batch of 500 ml is produced.

Safety Testing of Rabies Virus Recombinant Vaccines

The pathogenicity of the recombinant viruses is determined by injecting groups of ten 6–8 week old Swiss Webster mice i.c. with 10 μl or intramuscularly (i.m.) with 100 μl of 5 or 10-fold serial dilutions of each batch of virus preparation. The mice are observed for 4 weeks and the 50% lethal virus dose ($LD_{50}$) is calculated from the mortality rates obtained with the different virus dilutions. The pathogenicity index is calculated for each virus preparation by subtraction of the log of the $LD_{50}$/ml virus stock from the log of the virus titer of the stock (Pathogenicity index=log $LD_{50}$/ml minus log virus titer/ml). Recombinant virus vaccines with a pathogenicity index $<8^{-8.5}$ are regarded as safe.

Testing of Vaccine Potency Against Infection with DRV-7, RRV-27, and SRV-16 Using Parenteral Immunization Followed by i.c. Virus Challenge All new recombinant virus vaccines (R-DRV, R-RRV, R-SRV) as well as the already prepared vaccines (R-SHB18, R-B2c-333, R-N2cT, and SN10-333) are subjected to a modified NIH potency test. Groups of ten 6–8 week old Swiss Webster mice are inoculated i.m. with 100 μl of each of five 10-fold dilutions prepared from a particular vaccine batch. Ten days after vaccination, the mice are infected i.c. with 10 I.C. $LD_{50}$ of either DRV-7, RRV-27, or SRV-16 and then observed daily for a period of 4 weeks. The 50% effective dose ($ED_{50}$) of each vaccine is calculated from the percentages of survivorship obtained with the different vaccine dilutions. The tests identify the vaccines with the highest efficacy against infection with dog, raccoon, or skunk virus.

Testing of Vaccine Potency Against Infection with DRV-7, RRV-27, and SRV-16 Using Oral Immunization Followed by i.m. Virus Challenge Vaccines that yielded the highest efficacy after parenteral administration are further tested for their ability to induce protective immunity after immunization by the oral route. One hundred μl of serial vaccine dilutions containing $10^7$ to $10^4$ infectious units is installed into the buccal cavity of groups of ten mice. Oral immunization is also performed similarly with the commercial SAG-2 vaccine, which serves as a control. Ten and 20 days after immunization, the mice are bled and rabies VNA are determined. Thirty days after immunization, the mice are infected i.m. with 10 I.M. $LD_{50}$ of dog (DRV-7), raccoon (RRV-27), or skunk (SRV-16) rabies virus. These tests reveal whether oral immunization with virus-strain specific recombinant rabies vaccines induces a protective immune response which is superior to that obtained with already available vaccines.

Testing of Vaccine Stability

Since a live rabies virus vaccine must be very stable when used under field conditions, all vaccine batches are incubated at 24° C. and 37° C. for 10 days. Aliquots are removed every 24 h and the virus titer is determined. This test reveals whether the vaccine is stable under extreme environmental conditions (e.g., high ambient temperature).

Construction of Recombinant Rabies Virus Expressing Cytochrome c

Total RNA is isolated from Hela cells by the RNAzol B method (Biotex Laboratories, Inc., TX). The extracted RNA is reverse transcribed into cDNA by AMV reverse transcriptase (Promega) as described previously. (Morimoto, K., et al., *Proc. Natl. Sci USA* 95:3152–3156, 1998).

Cytochrome c cDNA is amplified using Taq DNA polymerase (Eppendorf) and primers Cyt 5 (5'-AAA CGTACGAATATGGGTGATGTTGAGAA-3', SEQ. ID. NO: 1, [BsiWI site underlined, start codon bold]) and Cyt 3 (5'-GAA GCTAGCTTACTCATTAGTAGCTTTTTTGAG-3', SEQ. ID. NO: 2, [Nhe I site underlined, stop codon bold]), to introduce BsiWI and NheI recognition sites before and after the cytochrome c coding region. The PCR product is then digested with BsiWI and NheI (New England Biolabs) and ligated into predigested pSPBN rabies virus vector, which contains single BsiWI and NheI sites between G and L genes. (Schnell, M. J., et al., *EMBO J.* 13:4195–4203, 1994). The resulting plasmid is designated as pSN-Cyto c (+). To inactivate the cytochrome c gene a stop codon is introduced into the cytochrome coding sequence 70 bp after the start codon by amplifying a cytochrome c fragment with Vent polymerase (New England Biolabs) and primers Cyt 5 and Cyt stop 3 (5'-GTGGCACTGGGATCACTTCATAAT-3', SEQ. ID. NO: 3, [stop codon bold]). A second fragment is amplified with Vent Polymerase using complementary primers, Cyt stop 5 (5'-ATTATGAAGTGATCCCAGTGCCAC-3', SEQ. ID. NO: 4, [stop codon bold]) and Cyt 3. Both fragments are annealed and amplified by Vent polymerase using primers Cyt 5 and Cyt 3. Then, the PCR product is digested and ligated into pSPBN the same way as described for pSN-Cyto c (+), which results in plasmid pSN-Cyto c (-).

A further aspect of the present invention is to engineer a recombinant rabies virus wherein the recombinant rabies virus incorporates both a glycoprotein gene from a heterologous virus (see supra) and a pro-apoptotic gene, such as cytochrome c. Further, this heterologous glycoprotein (encoded by the heterologous glycoprotein gene) may further contain a cytoplasmic tail that is from a different glycoprotein then is the ectodomain of the glycoprotein and/or a change in an amino acid within the glycoprotein such that the virus becomes less pathogenic/virulent. Standard and routine molecular biology methods are used to engineer the viruses of the present invention, such methods are well known to those of skill in the art.

Recovery of Recombinant Viruses

Recombinant viruses are rescued as described previously. (Morimoto, K., et al., *Proc. Natl., Sci. USA* 95:3152–3156, 1998; Morimoto, K., et al., *J. Virol.* 73:510–517, 1999). In brief, BSR-T7 cells are transfected with 5.0 µg of pSN-Cyto c (+) or pSN-Cyto c (-) together with 5.0 µg of pTIT-N, 2.5 µg of pTIT-P, 2.5 µg of pTIT-G and 2.0 µg of pTIT-L, which served as support plasmids using the Calcium Phosphate transfection kit (Stratagene). After 3 days incubation, supernatants are transferred onto BSR cells and incubated for 3 days at 37° C. The cells are examined for the presence of rescued virus by immunostaining with FITC-labeled anti-rabies virus N protein antibody (Centocor, Malvern, Pa.). The correct nucleotide sequences of the inserted genes are confirmed by RT-PCR and nucleotide sequencing.

Virus Infectivity Assay.

Infectivity assays are performed at 34° C. or 37° C. on monolayers of NA cells in 96-well plates as previously described. (Wiktor, T. J., et al., *Del. Biol. Stand.* 57:199–211, 1984). All titrations are carried out in triplicate.

Immunoprecipitation Analysis

BSR cells are infected with SN-Cyto c (-) or SN-Cyto c(+) at a m.o.i. of 5 and 24 h p.i. the infected cells are labeled with 50 µC [$^{35}$S] methionine for 2 h at 37° C. The resulting immunocomplexes are adsorbed to protein A-Sepharose beads (rProtein A Sepharose™ Fast Flow, Amersham Pharmacia Biotech, Piscataway, N.J.) and analyzed by SDS-15% PAGE as described previously. (Morimoto, K., et al., *J. Virol.* 73:510–517, 1999). The gel is dried and exposed to X-ray film.

Determination of Neutralizing Antibody (VNA)

Mouse sera are tested for the presence of VNA using the rapid fluorescent inhibition test (RFFIT) as described. (Wiktor, T. J., et al., *Dev. Biol. Stand.* 57:199–211, 1984). Neutralization titers, which are defined as the inverse of the highest serum dilution that neutralizes 50% of the challenge virus, are normalized to international units (IU) using the World Health Organization (WHO) anti-rabies virus antibody standard. Geometric mean titers (GMT) are calculated from individual titers of 10 mice that receive identical concentrations of the same vaccine virus. The significance of VNA titer differences in the different vaccination groups is determined by comparing the GMT VNA titers obtained with the different vaccine dilutions in a paired Student T test.

Immunofluorescence Staining and In Situ Terminal End Labeling of Rabies Virus-infected Primary Neuron Cultures Primary neuron cultures, which are prepared from the hippocampi of prenatal mice as described previously (Morimoto, K., et al., *J. Viol.* 73:510–517, 1999), are infected with SN-Cyto c (+) and SN-Cyto c (-) at a m.o.i. of 5 and incubated at 37° C. For immunofluorescence analysis the infected neuron cultures are fixed in 80% acetone at 48 h p.i. and subjected to a direct fluorescence stainining technique with fluorescein isothiocyanate (FITC)-labeled anti rabies N proteinspecific monoclonal antibody (Centocore, Malvern, Pa.) as described previously. (Morimoto, K., et al., *J. Virol.* 73:510–517, 1999). To detect DNA strand breaks indicative of apoptotic cell death the infected neurons are fixed with 4% paraformaldehyde at 48 h p.i and subjected to the terminal deoxynucleotidyltransferase-mediated dUTP nick endlabeling (TUNEL) assay as described. (Morimoto, K., et al., *J. Virol.* 73:510–517, 1999).

Pathogenicity Studies in Mice

Groups of 8–10 week-old female C3H mice (Taconic Farms, NY) are infected intranasally (i.n.) with 25 µl containing $5\times10^5$ infectious particles. After infection, the mice are observed daily for 4 weeks for appearance of clinical signs.

Immunization and Virus Challenge

Groups of 8–10 week-old female Swiss Webster mice (Taconic Farms, NY) are inoculated i.m. with 100 µl of serial 10-fold dilutions of live rabies recombinant viruses and 10 days later blood is collected from each mouse and the animals are infected i.c. with 10 µl containing 100 $LD_{50}$ of CVS-N2c. The mice are observed for 4 weeks for the development of clinical signs of rabies.

The significance of differences in survivorship between different vaccination groups is determined by comparing the survivorship rates achieved with the different vaccine dilutions in a paired Stutent T test. The $ED_{50}$ is calculated as described. (Wilbur, L. A., & Aubert, M. F. A., World Health Organisation, Geneva, Ch. 37, 360–368, 1996). To immunize mice orally 25 µl containing $10^6$ FFU of recombinant virus is instilled into the buccal cavity of groups of 10 mice; the mice were bled 2 weeks later and challenged with 100 $LD_{50}$ of CVS-N2c.

Results
Attenuation of Rabies Viruses Using Reverse Genetics and Site-directed Mutagenesis The primary requirements for any live vaccine is that the vaccine must be safe for the target species, as well as any other animal species that comes in contact with the vaccine, and the vaccine must be effective by the oral route in the target species. The target species is any mammal, including but not limited to, humans, dogs, foxes, raccoons, skunks, or any other free-ranging carnivore. Therefore, to be useful as a vaccine strain, the pathogenicity of the virus must be highly attenuated without affecting the antigenic and immunogenic properties of the virus.

Regarding the safety of live rabies virus vaccines, pathogenic rabies virus strains are modified so that they become completely non-pathogenic for immunocompetent mammals. It was previously shown that the rabies virus glycoprotein (G) is a major contributor to the pathogenicity of the virus. (Morimoto, K., et al., *J. Virol.* 73:510–517, 1999; Dietzschold, B., et al., *Proc. Natl. Acad. Sci. USA* 80:70–74, 1982; Seif, I., et al., *J. Virol.* 53:926–934, 1985). Several G-associated pathogenic mechanisms have been identified, for example, 1) G must interact effectively with cell surface molecules that mediate rapid virus uptake (Dietzschold, B., et al., *J. Virol.* 56:12–18, 1985; Lentz, T. L., et al,. *Proteins Struct. Funct. Genet.* 2:298–307, 1987; Thoulouze, M. I., et al., *J. Virol.* 72:7181–7190, 1998; Tuffereau, C., et al, *The EMBO Journal* 17:7250–7259, 1998); 2) G must interact optimally with the ribonucleoprotein-matrix (RNP-M) complex for efficient virus budding (Mebatsion, R., et al., *Cell* 84:941–951, 1996; Mebatsion, R., et al., *J. Virol.* 73:242–250, 1999; Morimoto, K., et al., *J.NeuroVirol.,* 6:373–381, 2000) and 3) expression levels of G must be highly controlled to prevent functional impairment of the infected neuron. (Morimoto, K., et al., *J. Virol.* 73:510–517, 1999).

The pathogenicity of a particular rabies strain is attenuated by the alteration of a determinant of the G protein that interacts with putative cell surface receptors. The pathogenicity of a particular rabies virus correlates with the presence of a determinant located within antigenic site III of the G protein. (Coulon, P., et al., *J. Gen. Virol.* 61: 97, 1982; Coulon, P., et al., *J. Gen. Virol* 64:693–696, 1983; Dietzschold, B., et al., *Proc. Natl. Acad. Sci. USA* 80:70–74, 1983). Change in the rabies pathogenicity corresponds to an amino acid substitution at position 333 of the G protein, which is arginine in the parent virus (e.g., ERA, CVS-11). Exchange of arginine 333 for glutamine or glycine results in a slowdown of virus uptake and a complete loss of pathogenicity of certain virus strains (e.g., ERA, CVS-11). (Dietzschold, B., et al., *Proc. Natl. Acad. Sci. USA* 80:70–74. 1982; Dietzschold, B., et al., *J. Virol.* 56:12–18, 1985). Entry of these non-pathogenic variants into the cell is decreased 7–8 fold when compared to the pathogenic parent. (Dietzschold, B., et al., Rhabdoviruses, in In: *Fields Virology*, 3rd edition, Fields, B. N., et al., eds., Lippincott-Raven Publishers, Philadelphia, 1137–1159, 1996). Furthermore, these attenuated, non-pathogenic variants are unable to spread from cell to cell in neuroblastoma cell cultures and have a much lower rate of spread throughout the brain of inoculated mice.

Alteration of the sequence of the G proteins cytoplasmic domain, such that the cytoplasmic tail of the glycoprotein gene is heterologous, will also attenuate the pathogenicity of a rabies virus strain. The cytoplasmic domain of the G protein plays an important function in virus budding through a specific interaction with the rabies virus matrix (M) protein. Deletion or structural changes within this domain result in a slowdown of viral morphogenesis, with the subsequent attenuation of pathogenicity. (Morimoto, K., et al., *J. NeuroVirol.,* 6:373–381, 2000).

Another way in which the pathogenicity of a rabies virus strain is attenuated is to increase the viral transcription and replication activity, which will lead to overexpression of viral proteins. Since viral proteins, in particular the rabies virus G protein, are cytotoxic, overexpression will result in apoptosis of the infected cells, thereby inhibiting the axonal/trans-synaptic virus spread, which is the major pathway of rabies virus infection. (Morimoto, K., et al., *J. Virol.* 73:510–517, 1999).

In the present invention, different modified rabies virus G genes are used to engineer rabies recombinant viruses. These recombinant viruses exhibited a marked decrease in virus uptake or virus egress and higher replication efficiency and G expression levels than wild-type viruses. (Morimoto, K., et al., *J. Neuro Virol.,* 6:373–381, 2000). These recombinant viruses were found to be non-pathogenic after i.m. inoculation but differed greatly in their ability to induce protective immunity. Their protective activity against infection with a particular challenge virus strain largely depended on the contribution of factors that are related to the G gene of the vaccine strain.

The rabies virus G protein, which carries the major determinants that are responsible for the pathogenicity of the virus, also contains the most important antigenic determinants that trigger a protective immune response. To attenuate the pathogenicity of a virus strain without affecting its antigenic and immunogenic properties, reverse genetics (Schnell, M. J., et al., *EMBO J.,* 13:4195–4203, 1994) and site directed mutagenesis are used to produce attenuated recombinant viruses. These procedures are well known to those skilled in the art. These recombinant viruses (see FIG. 1) were constructed by replacing the G protein gene of a cDNA clone of the non-neuroinvasive SN-10 strain with the G protein genes of the highly neuroinvasive strains SHBRV-18, CVS-N2c, and CVS-B2c. Infectious virus was then recovered from the different cDNA clones by using reverse genetics technology. (Schnell, M. J., et al., *EMBO J.,* 13:4195–4203, 1994). To further attenuate the recombinant viruses, site-directed mutagenesis was performed to change the arginine at position 333 of the G proteins of CVS-N2c and CVS-B2c to glutamine. In addition, the cytoplasmic domain of the CVS-N2c G protein was exchanged for the cytoplasmic domain of the SHBRV-18 G protein.

Pathogenicity of Rabies Recombinant Viruses

Figure 2:
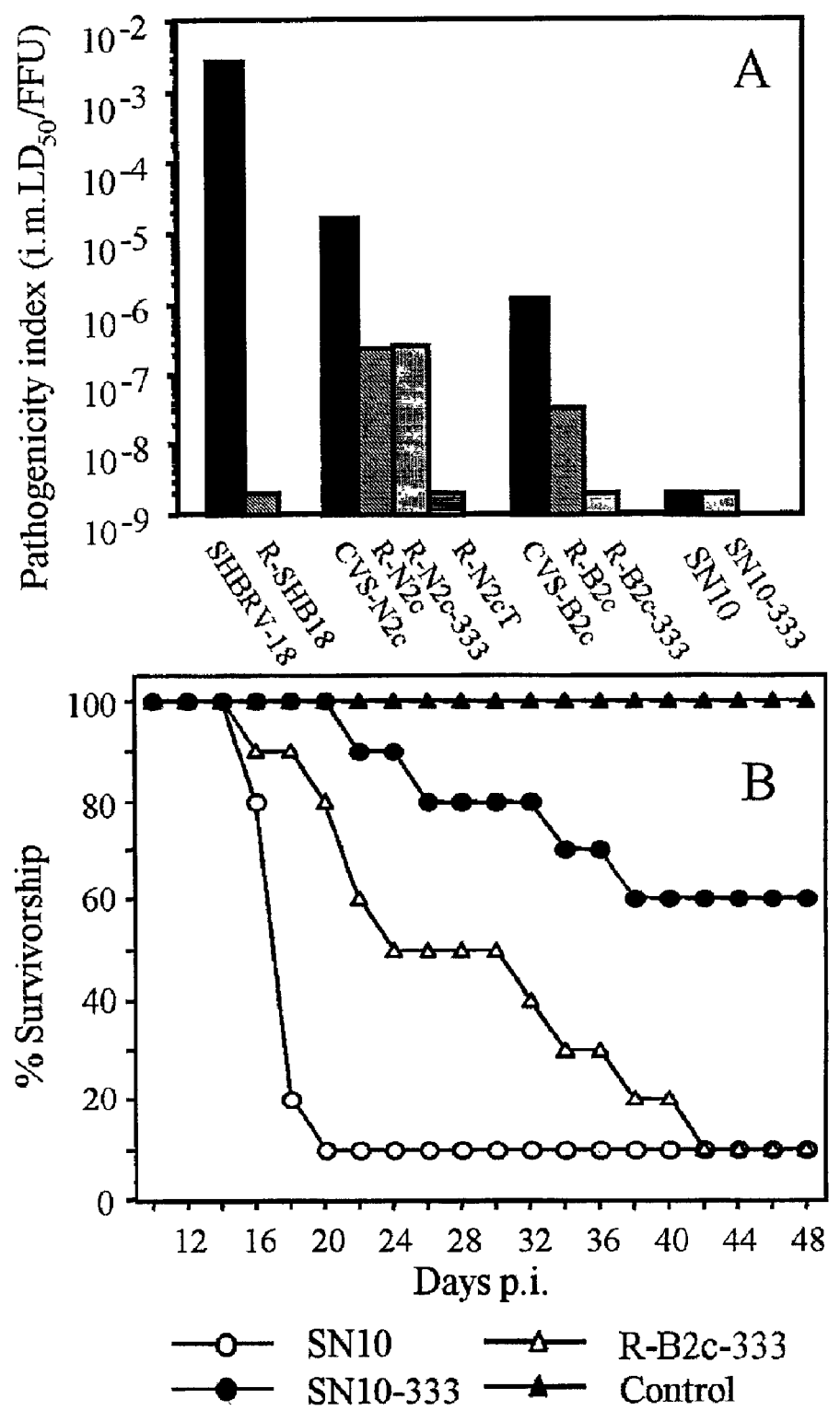

Following the rescue of the recombinant viruses, virus stocks are prepared from infected suckling mouse brains, and the pathogenicity indices of the virus stocks are determined (Pathogenicity index=log i.m $LD_{50}$/ml minus log virus titer/ml). FIG. 2 shows the pathogenicity indices of recombinant viruses in comparison with the corresponding parental viruses. Following i.m. infection of adult mice (FIG. 2), the recombinant virus R-SHB18 is highly attenuated as compared to the SHBRV-18 wild-type, while the recombinant viruses R-N2c and R-B2c are still pathogenic, although their pathogenicity indices are 70 or 30 times, respectively, lower than the pathogenicity indices of the corresponding parental viruses CVS-N2c and CVS-B2c.

Replacement of arg333 within G of R-B2c rendered this virus non-pathogenic (R-B2c-333, FIG. 2). In contrast, the same mutation in R-N2c G does not result in a reduction of pathogenicity (R-N2c-333, FIG. 2). On the other hand, a substantial reduction in the pathogenicity index is achieved by replacing the cytoplasmic domain of R-N2c G with that of SHBRV-18 G (R-N2cT, FIG. 2). If a direct i.c. administration is used, even attenuated viruses that do not kill when injected by a peripheral route will cause lethal disease in the majority of the infected animals. (Dietzschold, B., et al., Proc. Natl. Acad. Sci. USA 80:70–74, 1982; Seif, I., et al., J. Virol. 56:12–18, 1985). This is the case for R-SHB18, R-N2cT, and SN10 (Table 1). On the other hand, i.c. administration of $10^3$ infectious particles of R-B2c-333 caused only 10% mortality and an SN10 variant with an $arg^{333} \rightarrow gln^{333}$ mutation in G (SN10-333) is completely apathogenic. Notably, the genetic manipulations of the viral genome does not affect the ability of these viruses to grow in tissue cultures (BHK cells) to high titers (>$10^8$ FFU/ml). These experiments demonstrate the use of genetic technology to attenuate the pathogenicity of a rabies virus strain.

TABLE 1

Pathogenicity of rabies recombinant viruses

| Vaccine strain | % Mortality | |
| --- | --- | --- |
| | i.m.* | i.c.** |
| R-SHB18 | 0 | 90 |
| R-N2cT | 0 | 90 |
| R-B2c-333 | 0 | 10 |
| SN10 | 0 | 100 |
| SN10-333 | 0 | 0 |

Figure 3:
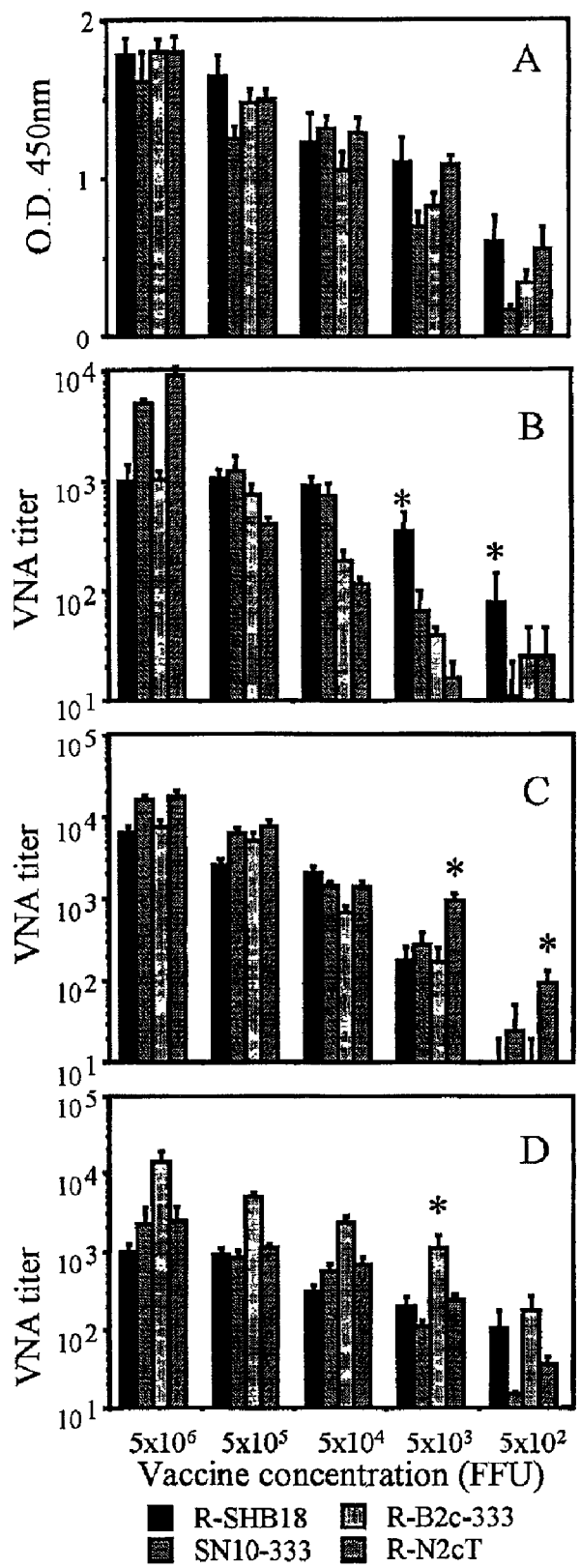
FIG. 3. Anti-RNP ELISA titers in mice immunized with live rabies recombinant viruses.

*groups of 20 mice were injected with $10^5$ FFU into the gastrocnemius muscle
**groups of 20 mice were injected with $10^3$ FFU into the brain Antibody Responses Following i.m. Vaccination with Attenuated Rabies Viruses The viruses used for vaccination share all proteins except for the G protein, therefore, the antibody response to the ribonucleoprotein complex (RNP) was assessed to determine the general index of virus replication with respect to antigenic mass and immunogenicity (RNP, FIG. 3). The amount of anti-RNP antibodies parallels the quantity of viral antigens produced after immunization. Anti-RNP titers obtained with the different vaccine strains are similar in mice that received the higher vaccine concentrations ($5\times10^6$ and $5\times10^5$ FFU) (FIG. 3). Anti-RNP antibody titers are somewhat higher in mice that were immunized with the lowest dose ($5\times10^2$ FFU) of R-SHB18 and R-N2cT than in those immunized with a comparable dose of SN10-333. These data show that the replication efficiency of the vaccine strains used is similar.

Efficacy of Live Rabies Virus Recombinant Vaccines

Rabies VNA are the major immune effectors against a rabies virus infection. (Cox, J. H., et al., Infect. Immun. 16:754–759, 1977). Nevertheless, rabies virus antigen-specific T helper cells (CD4+) and cytotoxic T cells (CD8+), as well as innate immune mechanisms, also play an important role in the protection against lethal rabies virus encephalitis. (Dietzschold, B. & Ertl, H. C., Critical Rev. Immunol., 10:427–439, 1991; Hooper, D. C., et al., J. Virol. 72:3711–3719, 1988).

VNA are almost exclusively induced by the rabies G protein. (Cox, J. H., et al., Infect. Immun. 16:754–759, 1977). In contrast, cellular immune responses are predominately triggered by the internal rabies virus proteins, in particular by the N and NS proteins. (Dietzschold, B. & Ertl, H. C., Critical Rev. Immunol., 10:427–439, 1991). Therefore, live rabies virus represents the best immunogen that will confer protective immunity. Currently, a few fixed rabies virus strains such as ERA, PM, LEP and SAD are used for the production of live or killed rabies virus vaccines. Although the various street rabies viruses that are associated with different mammalian species in different geographical locations around the world exhibit substantial genotypic differences (up to 20%), as well as antigenic differences (Smith, J. S., et al, Seminars in Virology 6:387–400, 1995), any of the currently used vaccines will induce protective immunity against these viruses after parenteral application, providing the potency of the vaccine is high enough. (Lodmell, D. L., et al., J. Virol. 69:4957–4962, 1995).

In the case of orally administered live vaccines, antigenic differences between the vaccine strain and the challenge virus will become a critical factor since the amount of vaccine that is taken up orally cannot be easily controlled. Therefore, sufficient immunity must be induced even when only a fraction of the vaccine dose is consumed. In order to achieve sufficient seroconversion with only a minimal dose of vaccine, the vaccine must meet several criteria. First, the antigenic makeup of the vaccine strain must closely match the antigenic structure of the challenge virus. Second, the vaccine virus must be able to replicate in the recipient so that a sufficient amount of viral antigen is presented to the immune system. Finally, the vaccine virus must replicate at sites and in tissues where optimal antigen presentation to the immune system will occur (e.g., skin, dendritic cells).

The difficulty in predicting whether a live virus vaccine will fulfill all of the above criteria requires that the actual potency of the vaccine be experimentally determined for the particular challenge viruses. In order to obtain preliminary information regarding the efficacy of live rabies virus vaccines, the potency of four attenuated genetically engineered rabies recombinant viruses (SN-10-333, R-B2c-333, R-N2c-T, and R-SHB-18) against 3 different challenge viruses was determined. The challenge viruses used are CVS-N2c, which is the high pathogenicity variant of the mouse brain adapted CVS-24 strain (Morimoto, K., et al., Proc. Natl. Acad. Sci. USA 95:3152–3156, 1998); the SHBRV-18 strain, a highly pathogenic silver-haired bat-associated street rabies virus; and CVS-B2c, the mouse adapted low pathogenicity strain.

All four vaccines are adjusted to the same content of infectious units (FFU/ml) and groups of 10 Swiss Webster mice were immunized i.m. with one of five 10-fold dilutions of each vaccine. Ten days after immunization, the animals are bled and infected i.c. with 100 $LD_{50}$ of one of the three challenge viruses. The i.c. challenge is chosen because it is the most rigorous and reliable rabies virus challenge infection that is regularly used in the National Institute of Health (NIH) vaccine potency test.

Figure 4:
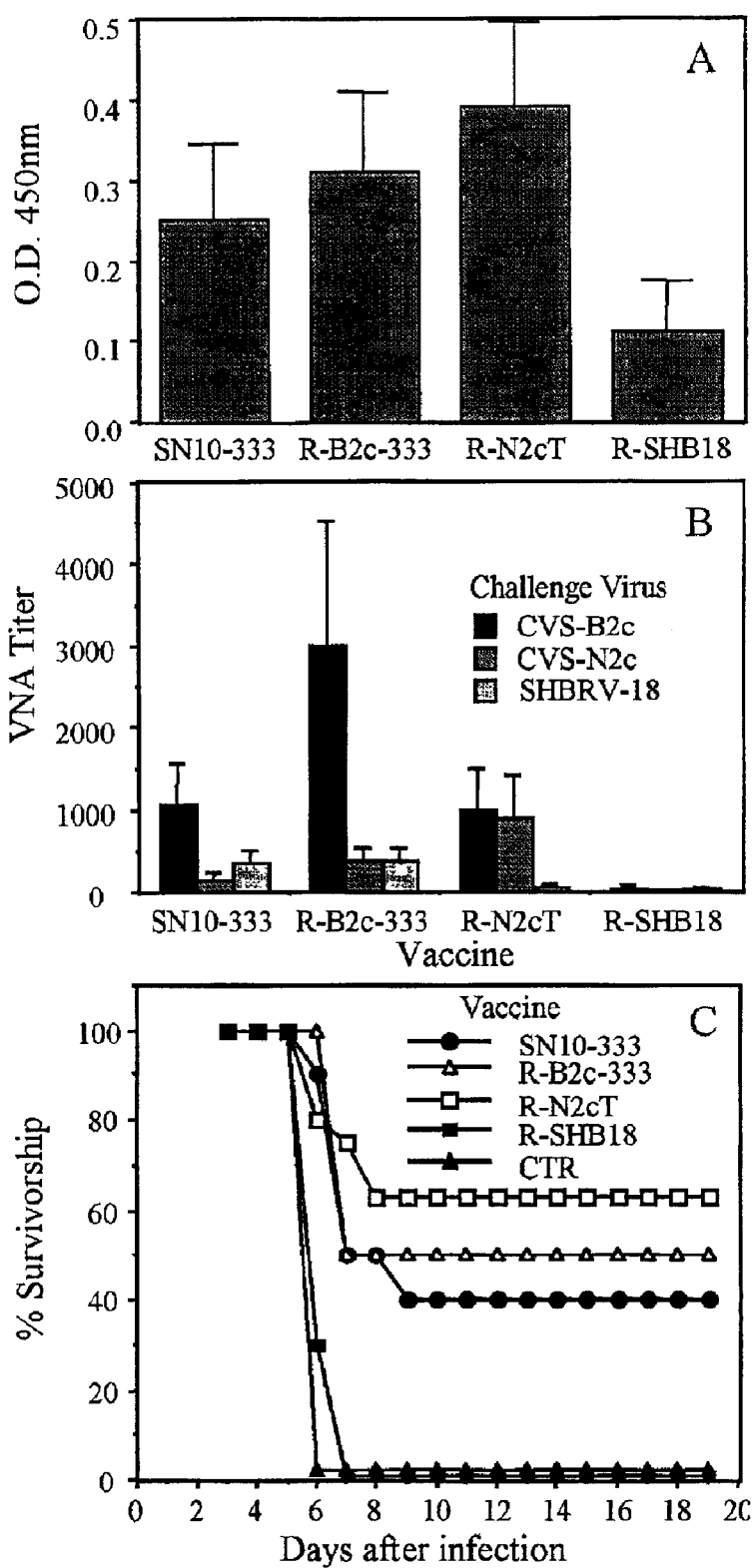
FIG. 4. Induction of neutralizing antibody against CVS-B2c (A), CVS-N2c (B), and SHBRV-18 (C) in mice immunized i.m. with different concentrations of R-SHB18, SN-10-333, R-B2c-333, and R-N2c-T.

FIG. 4 shows the VNA titers against CVS-B2c (A), CVS-N2c (B), and SHBRV-18 (C) of mice immunized with different concentrations of R-SHB18, SN10-333, R-B2c-333, and R-N2cT. At the higher vaccine concentrations ($5\times10^6$ and $5\times10^5$ FFU), all four vaccines induced high VNA titers against all of the three challenge viruses used in the test. At the lower vaccine concentration ($5\times10^3$ and $5\times10^2$ FFU), the VNA titers of sera from mice immunized with R-N2c-T are highest against the homologous CVS-N2c challenge virus. However, in mice immunized with R-SHB18 or R-B2c-333, titers obtained at the lower vaccine concentrations are actually higher against heterologous viruses. In this case, highest VNA titers against CVS-B2c and SHBRV18 are produced in mice immunized with R-SHB-18 or R-B2c-333. These data demonstrate that antigenic homology of the G proteins between vaccine strain and challenge virus does not necessarily result in the production of the highest VNA titers against the challenge virus.

Protection Conferred by Infection with Recombinant Rabies Viruses

Figure 5:
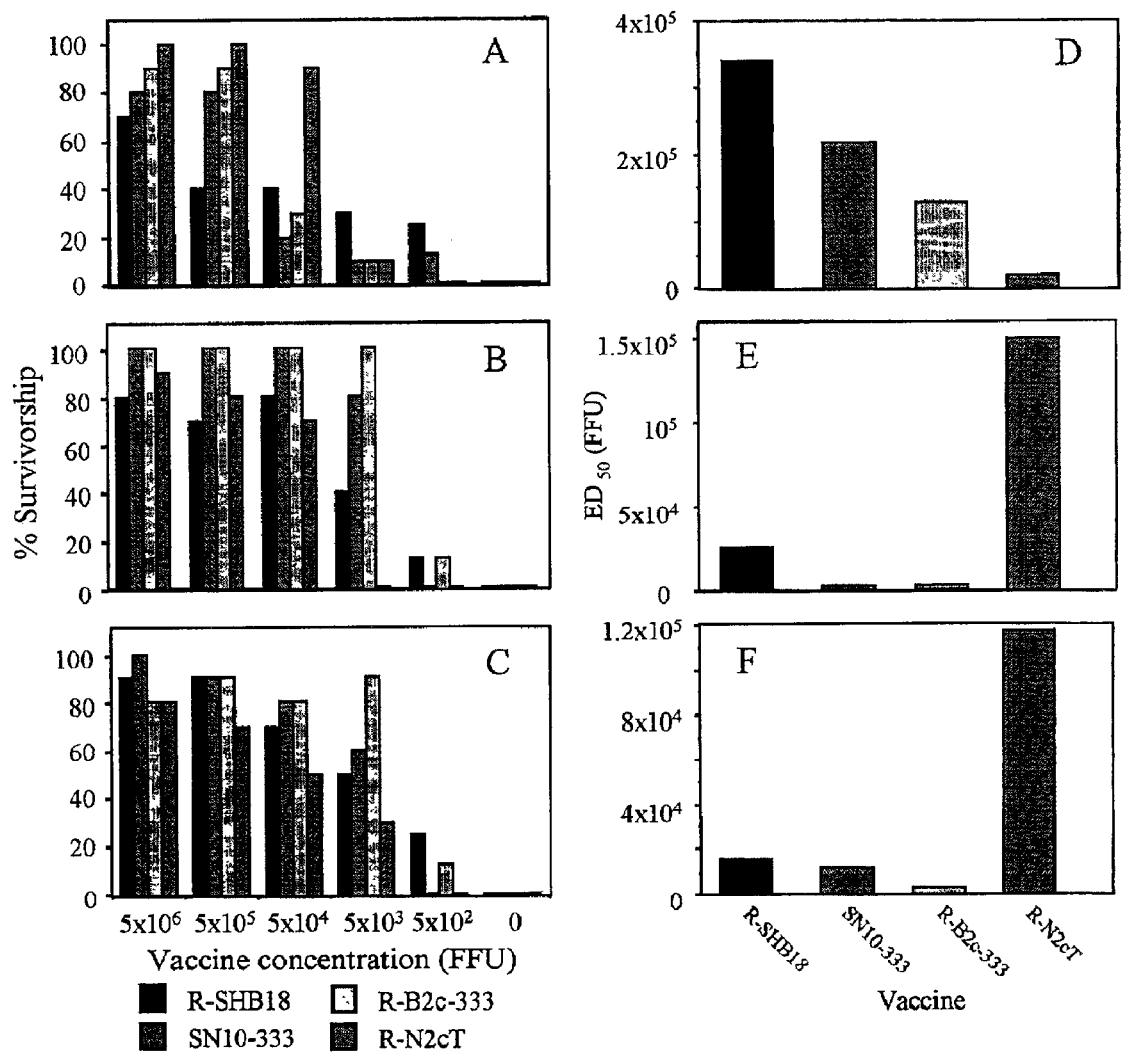
FIG. 5. The survivorship in groups of mice immunized with the four attenuated experimental live vaccines R-SHB-18, SN-10-333, R-B2c-333, and R-N2c-T and challenged intracranially (i.c.) with CVS-N2c (A), DRV-7 (B), and SHBRV-18 (C) The potency of rabies virus recombinant vaccines is determined using an i.c. challenge infection with CVS-N2c (D), DRV-7 (E) and SHBRV-18 (F). The $LD_{50}$s for the different vaccines are calculated from the rates of survivorship obtained with the different vaccine dilutions shown in FIG. 5A–C.

To determine the level of protection against a lethal challenge conferred by the immune response to vaccination with SN10-333, R-B2c-333, R-N2cT, and R-SHB18, immunized mice were challenged by i.c. infection with the three highly virulent rabies virus strains CVS-N2c, DRV-7, SHBRV-18 (FIGS. 5A–C). The survivorship in groups of mice immunized with different doses of the recombinant viruses and infected i.c. with each of the three challenge viruses is shown in FIG. 5. In the case of a CVS-N2c challenge infection (FIG. 5A), the highest survivorship was found in the groups of mice immunized with the homologous R-N2c-T vaccine. The $ED_{50}$ of R-N2cT immunization against CVS-N2c is 50, 100 and 155 times lower than the $ED_{50}$ of R-B2c-333, SN-10-333, and R-SHB18, respectively (FIG. 5D), demonstrating the superior protective activity of vaccination with homologous G. On the other hand, immunization with heterologous R-B2c-333, rather than R-SHB18 with homologous G, resulted in the lowest mortality following challenge infection with SHBRV-18 (FIG. 5C). The $ED_{50}$ of R-B2c-333 was 33, 3, and 4 times lower those of R-N2cT, SN10-333, and R-SHB18, respectively (FIG. 5F). R-B2c-333 also conferred the best protection against challenge with the dog-associated rabies virus strain DRV-7 (FIG. 5B). Notably, as little as $5 \times 10^3$ virus particles of R-B2c-333 were sufficient to protect 100% of the animals against infection with DRV-7, while even $5 \times 10^6$ particles of R-SHB-18 or R-N2cT conferred only incomplete protection. The results of these protection experiments clearly demonstrate marked differences in the potency of live virus vaccines, which are in some cases, but not always, related to G homology. The protective activity of a particular vaccine depends largely on the nature of the vaccine and the challenge virus. A comparison of the data in FIGS. 4B and 5A reveals that VNA titers do not necessarily correlate with in vivo protection, particularly with respect to immunization with R-SHB18.

Phenotypic Characterization of Recombinant Viruses In Vitro

Figure 6:
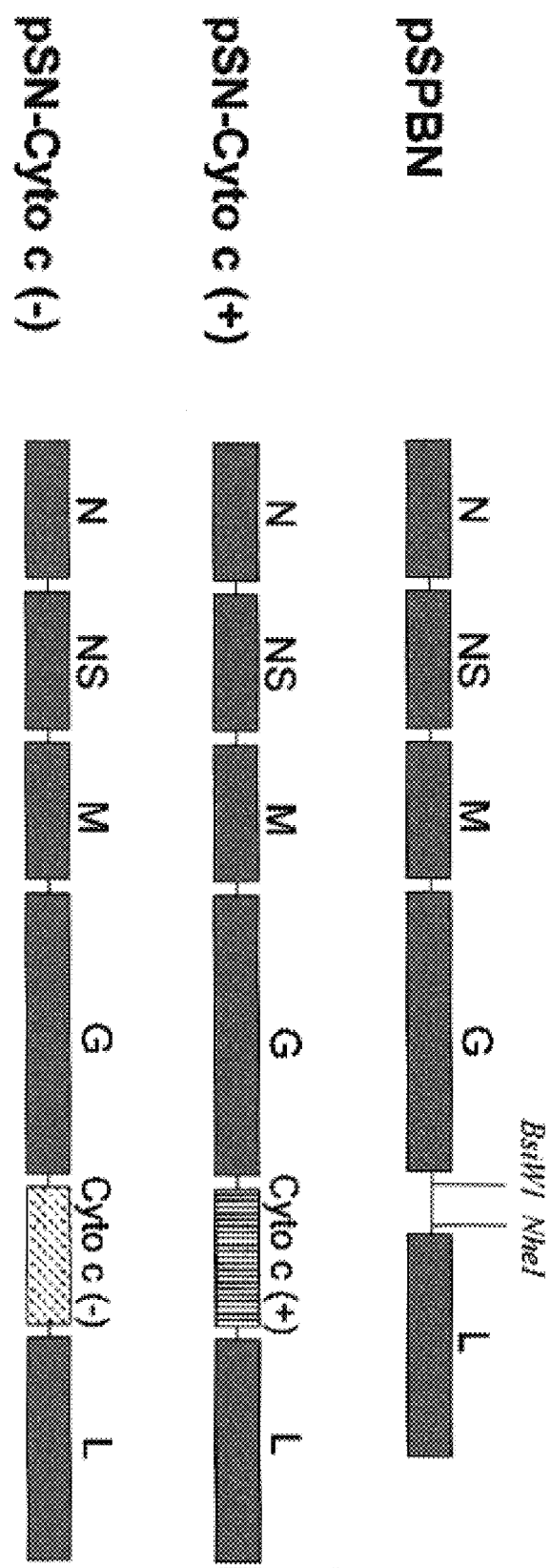
FIG. 6. Diagram showing the design of rabies virus cytochrome c recombinant viruses. The pSPBN vector is derived from SN-10 by removing the ψ gene and introduction of a BsiWI and a Nhe I site between the G and L genes. Human cytochrome c cDNA is amplified by PCR and after introduction of BsiWI and a Nhe I sites ligated into pSPBN, which results in pSN-Cyto c(+). To construct pSN-Cyto c (−) a stop codon is introduced into the cytochrome c gene 70 bp after the start codon.

To test the hypothesis that apoptosis attenuates the pathogenicity of a rabies virus and probe the possible mechanisms involved, a rabies recombinant virus is engineered to expresses cytochrome c (pSN-Cyto c(+) FIG. 6). To ensure that expression of cytochrome c, rather than the presence of a foreign nucleotide sequence, accounts for any observed effects, a recombinant virus in which an inactivated cytochrome c gene is inserted is also engineered (pSN-Cyto c(−) FIG. 6). The cytochrome c is inactivated by insertion of a stop codon near the 5' end of the cytochrome c gene.

Figure 7:
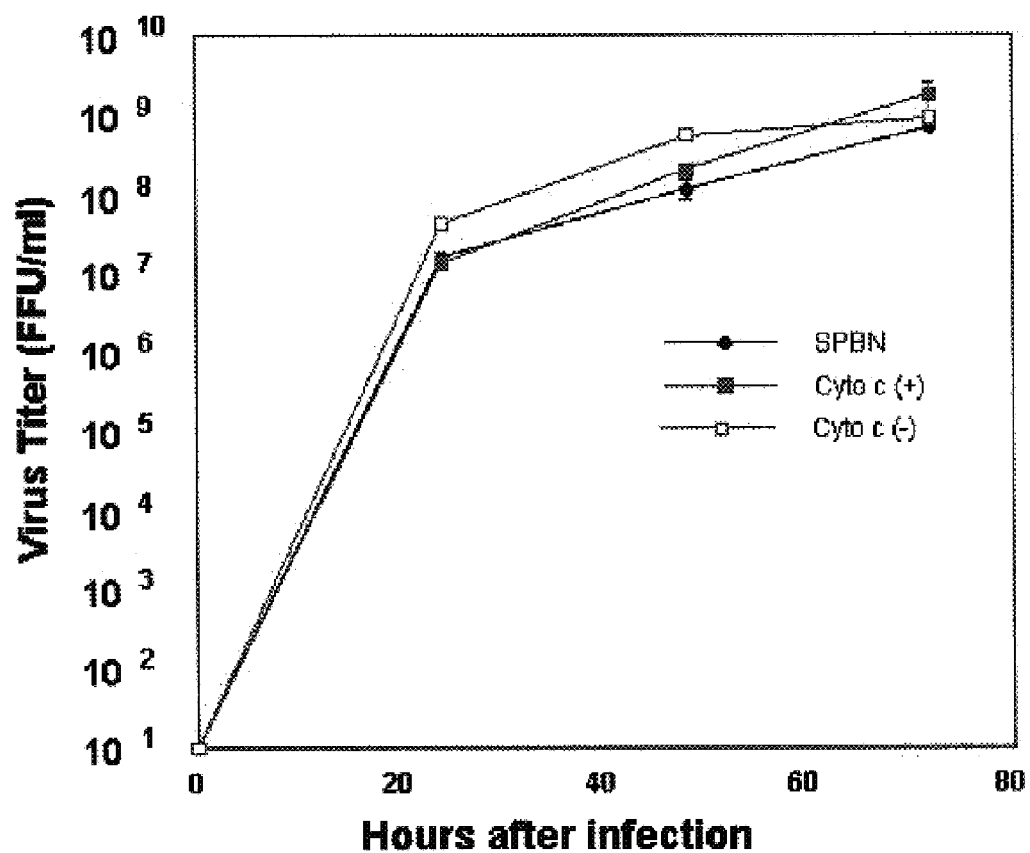
FIG. 7. Rate of virus production of recombinant and parental rabies virus strains in BSR cells. The cells are infected with SPBN (close circles), SN-Cyto c (+) (closed squares) and SN-Cyto c (−) (open squares) at an m.o.i. of 2.5 and incubated at 37° C. Viruses are harvested at days 1, 2, 3 after infection, and titrated by a fluorecscent staining method. Error bars indicate the standard error of the mean of six virus titer determinations.
Figure 8:
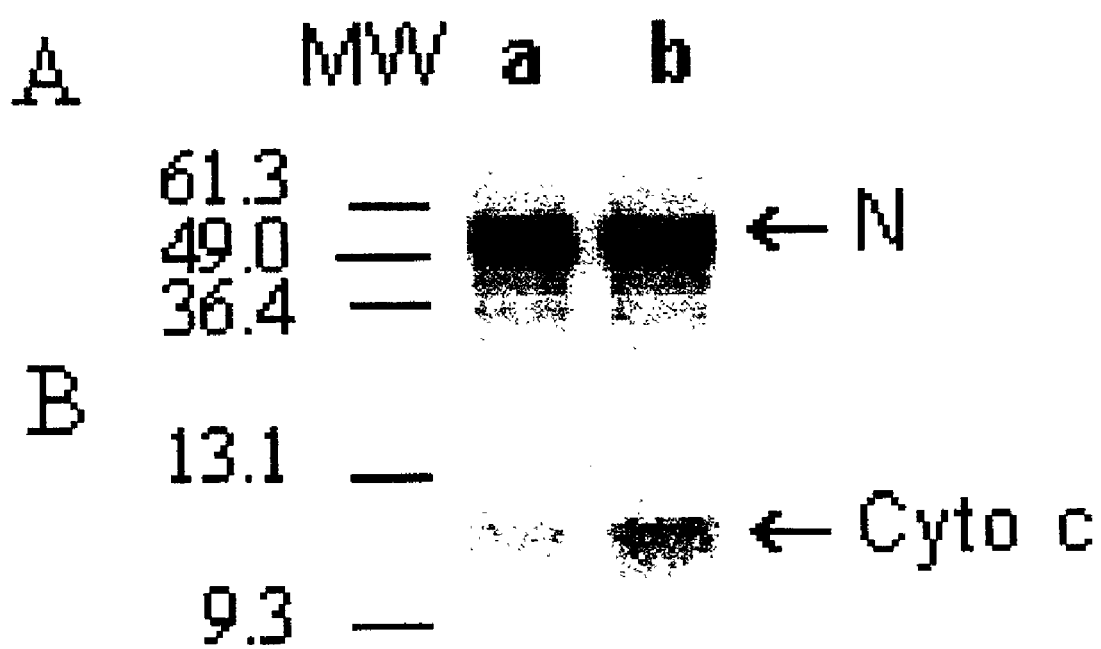
FIG. 8. Immunoprecipitation analysis of the rabies virus N protein and cytochrome c in mouse neuroblastoma cells infected with either SN-Cyto c (−) (lane a) or SN-Cyto c(+) (lane b). The infected cells are labeled with 50 µCi per ml for 2 h at 37° C. Then the cells are lysed and 100 µl of lysate is subjected to immunoprecipitation with either a polyclonal anti-rabies N protein (panel A) or an anti-cytochrome c (panel B) antiserum. Immune complexes are analyzed by SDS-10% PAGE. The gel is dried and exposed to X-ray film.

To determine whether the insertion of foreign genes affects virus replication, the time course of parental and recombinant virus production in NA cells is compared. FIG. 7 shows that SN-Cyto c (+) and SN-Cyto c (−) have similar rates of virus production as compared to the parental strain SPBN. Immunoprecipitation is performed to analyze the expression of cytochrome c in NA infected cells. While the levels of N-protein expressed in SN-Cyto c (+)-infected cells do not differ from those detected in SN-Cyto c(−)-infected NA cells, the expression levels of cytochrome c is markedly higher in SN-Cyto c(+)-infected NA cells (FIG. 8).

Figure 9:
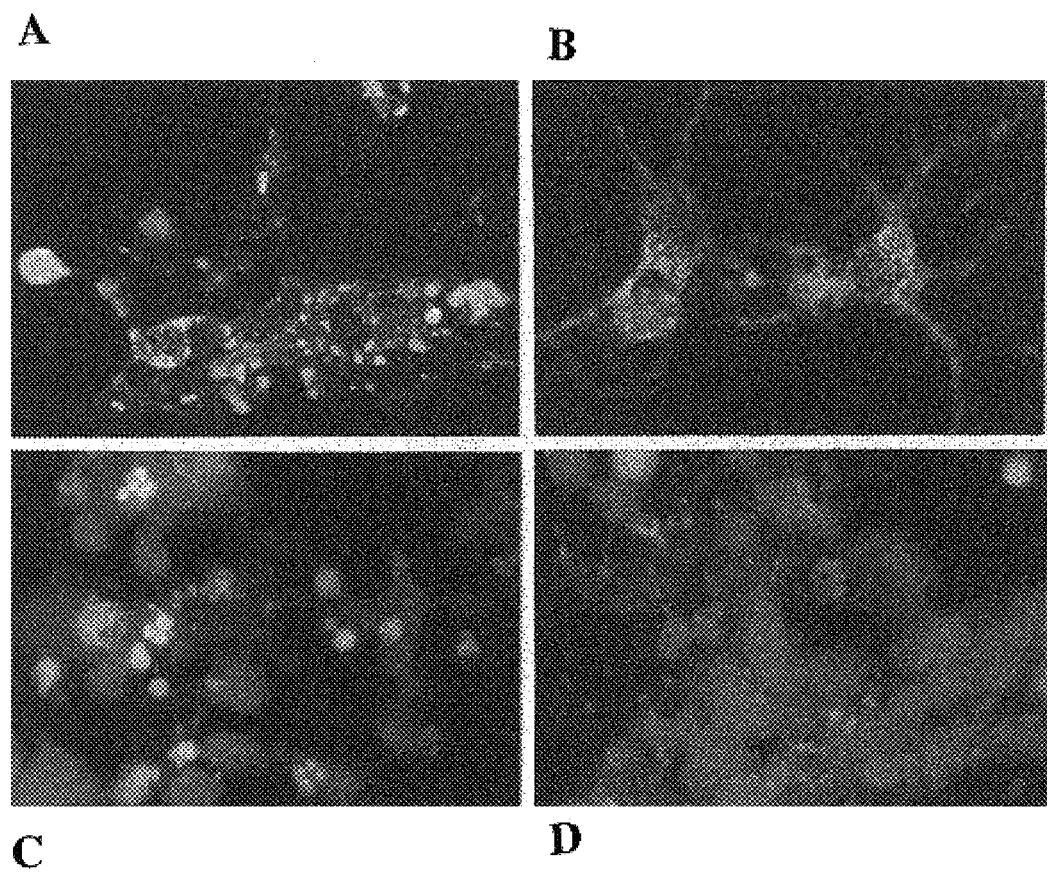
FIG. 9. Immunofluorescence analysis of the rabies virus N protein (panels A and B) and TUNEL analysis (panels C and D) of primary neuron cultures infected with SN-Cyto c (−) (B, D) or SN-Cyto c (+) (A, C) and examined 48 h post-infection (p.i.).

Immunofluorescence analysis of N protein expression in SN-Cyto c(+)-infected primary hippocampal neuron cultures at 48 h p.i. show large N protein-positive inclusion bodies in the cell body cytoplasm and almost no N protein-specific staining in neuronal processes (FIG. 9A). In contrast, SN-Cyto c(−)-infected neurons show a more fine granular N-protein staining pattern, which extends into the neuronal processes (FIG. 9B). TUNEL staining of infected neuron cultures reveals a large number of TUNEL-positive nuclei in SN-Cyto c(+)-infected neurons at 48 h p.i. (FIG. 9C) while only a few TUNEL-positive nuclei are detected in SN-Cyto c(−)-infected neurons at 48 h p.i. (FIG. 9D).

Effect of Cytochrome c Overexpression on Pathogenicity

Figure 10:
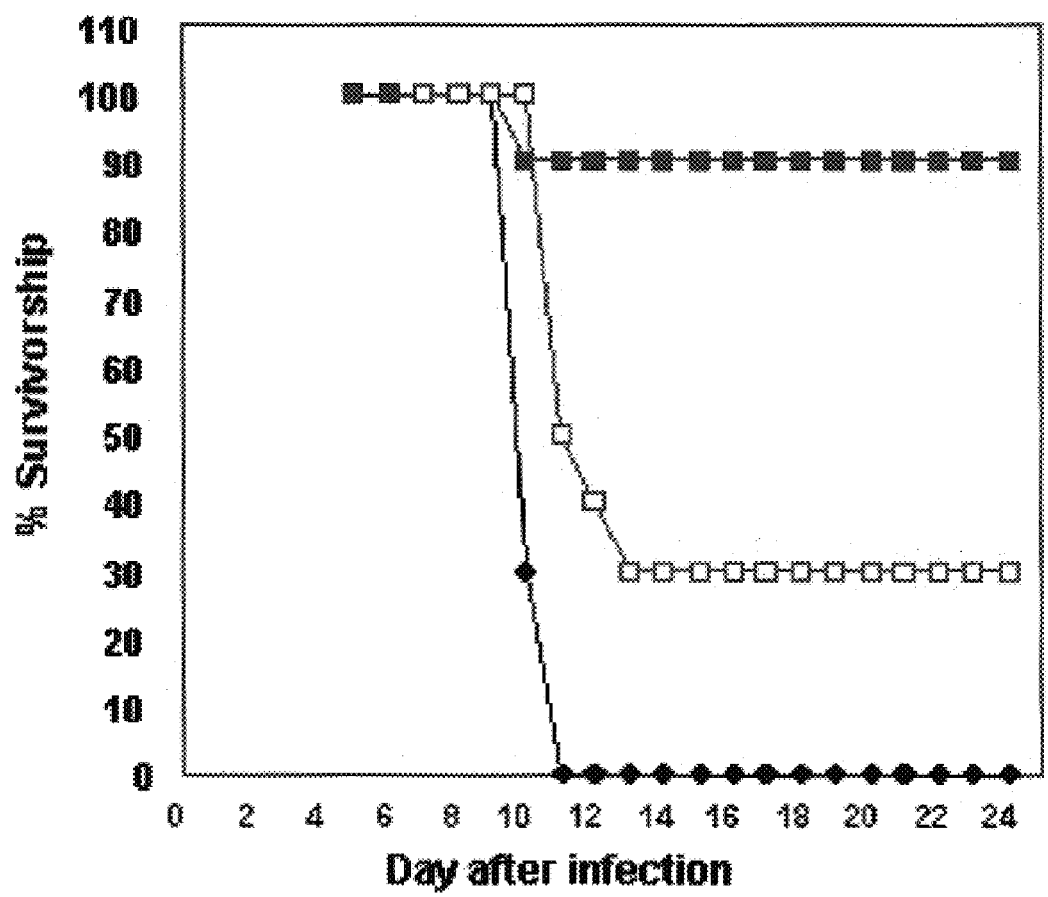
FIG. 10. Survivorship of mice intranasally infected with $10^6$ FFU of SPBN (closed circles, dotted line), SN-Cyto c(−) (open squares) or SN-Cyto c (+) (closed squares). Groups of 10 mice are infected with each virus and the animals are observed for 4 weeks for the development of clinical signs of rabies.

To examine the effect of overexpression of cytochrome c, parental SPBN virus, SN-Cyto c(+) and SN-Cyto c(−) are compared for their ability to cause a lethal rabies virus encephalitis in immunocompetent adult C3H mice. All these rabies viruses are essentially nonpathogenic when inoculated i.m.. On the other hand, 100% and 70% of mice infected intranasally (i.n.). with $10^6$ FFU of SPBN or SN-Cyto c(−), respectively, succumb to rabies virus infection. In contrast, only 10% of mice infected i.n. with the same FFU of SN-Cyto c(+) died from lethal rabies encephalitis (FIG. 10).

Figure 11:
FIG. 11. Immunohistochemical analysis for rabies virus N protein in coronal sections through the hippocampus of mice infected intranasally with SPBN (A), SN-Cyto c(−) (B) or SN-Cyto (+) (C).
Figure 11:
Figure 11:

Immunohistological analysis of infected mouse brains at 10 days after i.n. infection reveal the presence of large numbers of N protein-positive neurons in almost all areas of brains infected with the SPBN wild-type virus (FIG. 11). Lesser numbers of infected neurons are detected in SN-Cyto c (−)-infected brains and only a very few infected neurons are seen in mouse brains infected with SN-Cyto c(+). These data demonstrate that the mortality resulting from infection with the different wild-type and recombinant viruses correlates with their ability to invade the brain following i.n. infection.

Effect of Cytochrome c Overexpression on Immunity

Figure 12:
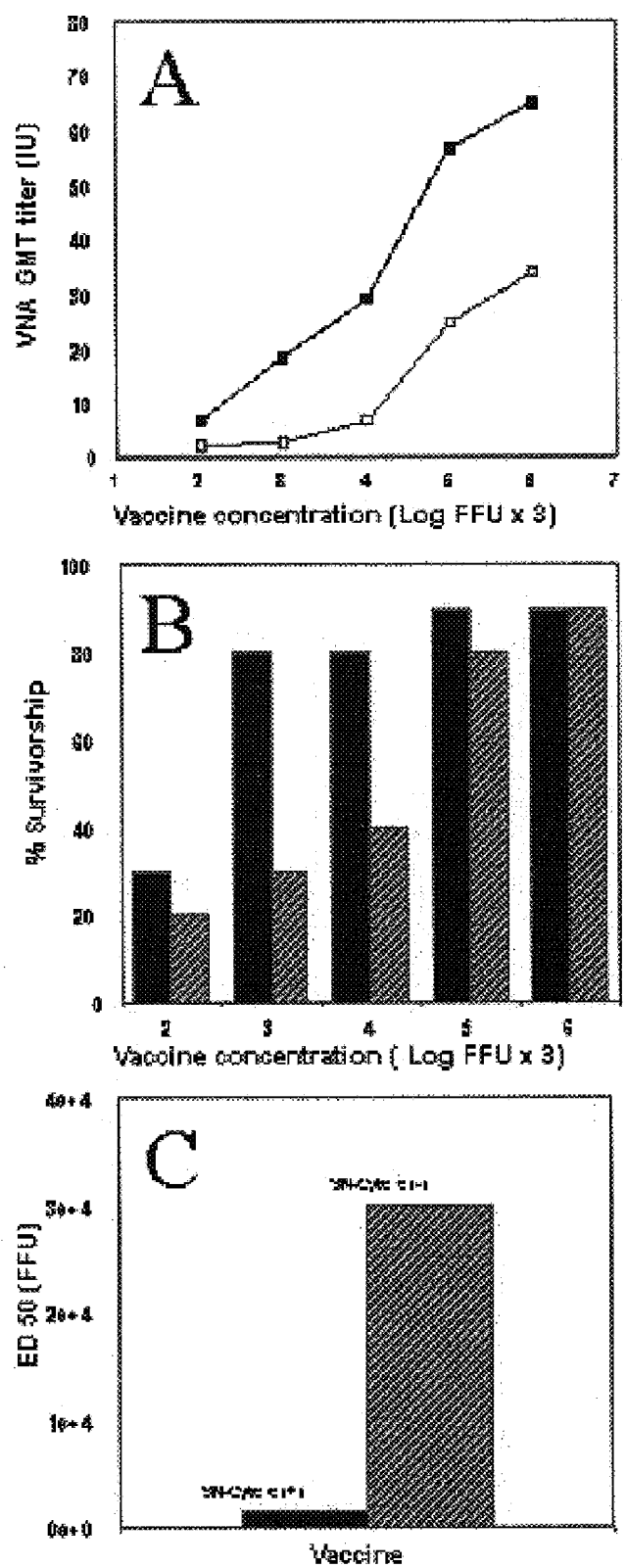
FIG. 12. Immunogenicity of SN-Cyto c (+) and SN-Cyto c (−) after intramuscular immunization. Groups of 10 mice are immunized with serial 10-fold vaccine dilutions, and 10 days later the mice are bled and VNA titers of mice immunized with of SN-Cyto c (+) (closed squares) and SN-Cyto c (−) (open squares) are determined using the RFFIT test (Wiktor, T. J., et al., *Dev. Biol. Stand.* 57:199–211, 1984) and CVS-B2c as challenge viruses. Titers are normalized to international units (IU) using the WHO standard, and represented as geometric mean titers (FIG. 12A). Two weeks after immunization the mice are infected i.c. with 100 LD50 of CVS-N2c and observed for 4 weeks. Survivorships in groups of mice immunized with SN-Cyto c (+) (black columns) and SN-Cyto c (−) (shadowed colums) are recorded (FIG. 12B). The $ED_{50}$s (FIG. 12C) are calculated from the survivorship rates in the different vaccination groups as described. (Wiktor, T. J., et al., *Dev. Biol. Stand.* 57:199–211, 1984).

Since rabies VNA are the major immune effectors against a lethal rabies virus infection, the VNA responses following intramuscular inoculation of serial dilutions of SN-Cyto c(+) and SN-Cyto c(−) are compared. FIG. 12 shows that the geometric mean VNA titers induced by SN-Ctyo c(+) are, on average, 3.5 times higher as compared to the titers induced by SN-Cyto c(−). Paired student t-test analysis of the VNA titers shown in FIG. 12 indicates that the differences in VNA titers are highly significant (p=0.016). To determine whether the differences in VNA titers induced by both recombinant viruses are reflected in protection, mice vaccinated with serial dilutions of SN-Cyto c(+) and SN-Cyto c(−) are challenged i.c. with 10 $LD_{50}$ of CVS-24 virus. FIG. 12A shows that the survivorship of mice immunized with SN-Cyto c(+) is significantly higher (on average, 1.7 times, p=0.009) than the survivorship of SN-Cyto c(−)-immunized mice. The $ED_{50}$ calculated from the mortality rates in the different vaccine dilution groups shown in FIG. 12A reveal that the efficacy of SN-Cyto c(+) is 20 times higher than the efficacy of SN-Cyto c(−), clearly demonstrating that overexpression of cytochrome c by a rabies recombinant virus strongly enhances the protective immunity against rabies. The present invention therefore serves a long sought, yet unfulfilled need for an effective rabies virus vaccine.

Pharmaceutical Compositions

The present invention also provides pharmaceutical compositions. Such compositions comprise a therapeutically effective amount of the recombinant rabies virus vaccine and a pharmaceutically acceptable carrier or excipient. Such a carrier includes but is not limited to saline, buffered saline, dextrose, water, glycerol, ethanol, and combinations thereof. The carrier and composition can be sterile.

Administration can be intramuscularly, intravenous, intracranial, intranasal, and most preferably orally.

Discussion

A number of effective killed and live attenuated rabies vaccines are currently available. (Aubert, M. F. A., et al., Oral wildlife rabies vaccination field trials in Europe with recent emphasis on France. In: *Lyssaviruses*, Rupprecht, C. E., et al., eds. Springer-Verlang, Berlin, Heidelberg, New York, 219–243, 1994; Fu, Z. F., et al., Improved vaccines against rabies, In: New Generation Vaccines, Second Edition, M. M. Levine, et al., eds., Marcel Dekker, Inc. New York, 607–617, 1997). Nevertheless, large reservoirs of different rabies virus strains persist in wild and domestic animals. (Rupprecht, C. E., et al., *Emerging Infectious Diseases* 1(4):107–114, 1995; Smith, J. S., et al., *Seminars in Virology* 6:387–400.15, 1995). The major reason for this are difficulties, both technically and economically, in vaccinating these animals. For the most part, killed vaccines are not suitable for wild and stray animals because delivery of an appropriate antigenic mass is impossible to guarantee by the necessary baiting procedures. Only live vaccines confer sufficient herd immunity to eliminate the reservoir.

An ideal vaccine will protect against infection with all of the street rabies viruses that are associated with different mammalian species in diverse geographical locations. As described above, antigenic differences between vaccine strains and the challenge viruses only become a critical factor in vaccine failure when low doses of vaccine are administered. Delivery of an appropriate vaccine dosage can only be guaranteed by parenteral administration. In this case, current vaccines licensed for use in humans and animals will confer protective immunity against a variety of street rabies virus strains. (Lodmell, D. L., et al., *J. Virol.* 69:4957–4962, 1995). Since the amount of vaccine that is orally consumed cannot be easily controlled by bait delivery, protective immunity must be induced even when only a fraction of the vaccine dose is taken up. In order to achieve sufficient immunoprotection with only a minimal amount of vaccine, the following criteria must be fulfilled: 1) the antigenic composition of the vaccine strain and the challenge virus should be closely related; 2) the vaccine virus should be able to replicate sufficiently in the recipient so that enough viral antigen is presented to the immune system; and 3) the vaccine virus must replicate at sites and in tissues where optimal antigen presentation to the immune system will occur.

In addition to having optimal efficacy, safety is the most important criteria of any live vaccine. Pathogenicity is not only a function of the virus but is also largely dependent on the site of infection and the immune status of the host; therefore, even the most attenuated rabies viruses can potentially cause a lethal encephalomyelitis (Hooper, D. C., et al., *J. Virol.* 72:3711–3719, 1998; Yang, C. & Jackson, A. C. *J. Gen. Virol.* 73:895–900, 1992). As viral neuroinvasiveness is the major element of the pathogenesis of rabies, live rabies viruses suitable for vaccines must be crippled in this ability. Ideally however, a vaccine candidate virus will be unable to spread within the CNS after direct i.c. injection.

The present invention describes several distinct genetic manipulations that affect spread of a rabies virus to the CNS without affecting the viral immunogenicity. Immunogenicity is preserved by utilizing the G protein from pathogenic rabies viruses. However, although G is the most important rabies virus protein responsible for the induction of protective immunity, G also contains major pathogenicity determinants. (Morimoto, K., et al., *J. Virol.* 73:510–517, 1999; Dietzschold, B., et al., *Proc. Natl. Acad. Sci. USA* 80:70–74, 1982; Seif, I., et al., *J. Virol.* 53:926–934, 1985; Morimoto, K., et al., *J. NeuroVirol.*, 6:373–381, 2000). For instance, an attenuated rabies virus strain can be made more pathogenic by replacing its G protein with that of CVS-N2c, a highly neuroinvasive strain. Nevertheless, the recombinant virus does not have the full pathogenicity of the wild type virus. (Morimoto, K., et al., *J. NeuroVirol.*, 6:373–381, 2000). One explanation for the reduction in pathogenicity is that the recombinant viruses have a higher transcription/replication rate and cytotoxicity that are characteristics of less pathogenic rabies virus strains. (Morimoto, K., et al., *J. Virol.* 73:510–517, 1999; Morimoto, K., et al., *J. NeuroVirol.*, 6:373–381, 2000).

The recombinant virus R-SHB18, which was constructed with G of the highly neuroinvasive SHBRV-18, unlike its wild-type parent, was completely apathogenic after i.m. injection. In this case, budding efficiency was severely impaired due to a mismatch between G and the RNP-M complex. It has previously been shown that a mismatch between the cytoplasmic domain of G and the RNP-M complex is sufficient to attenuate the virus. For example, replacement of the cytoplasmic domain of G from R-N2c with that of SHBRV-18 rendered the virus apathogenic when administered i.m.. (Morimoto, K., et al., *J. NeuroVirol.*, 6:373–381, 2000).

A major determinant of rabies virus pathogenicity involved in virus uptake is located at antigenic site III of G. (Dietzschold, B., et al., *Proc. Natl. Acad. Sci. USA* 80:70–74, 1982; Sief, I., et al., *J. Virol.* 53:926–934, 1985). In an attempt to achieve further attenuation, site-directed mutagenesis was used to exchange the arginine at position 333 of G for glutamine. This substitution completely abolished the pathogenicity of SN10 and reduced that of R-B2c dramatically, but had no effect on either the i.m. or i.c. pathogenicity of R-N2c. This indicates that distinct pathogenic attributes are functional in different rabies viruses and targeting of a single determinant of pathogenicity is not sufficient to design a live vaccine strain.

Rabies virus strains differ significantly in their ability to infect neuronal and non-neuronal cells. (Morimoto, K., et al., *J. NeuroVirol.*, 6:373–381, 2000; Dietzschold, B., et al., *J. Hum. Virol.* In press, 2000). This is reflected in quantitatively and qualitatively different immune responses to infection with various rabies virus strains. The present invention utilized G from viruses with distinct neurotropisms to generate recombinant viruses that retain the tissue specificity of the parent virus. (Morimoto, K., et al., *J. Neuro Virol.*, 6:373–381, 2000). The fact that similar antibody responses to RNP are elicited by infection with these recombinants indicates that antigen production by these viruses is comparable.

The overall quantities of neutralizing antibodies produced also appears to be equivalent, although there are some differences in specificity for the in vitro challenge viruses. Importantly, the highest protection against a particular challenge virus was not necessarily dependent on G homology between vaccine strain and challenge virus. While R-N2cT infection protected best against infection with CVS-N2c, the R-B2c-333, rather than the R-SHB18, protected best against challenge with SHBRV-18. Neither the VNA response pattern nor the homology between the Gs of the vaccine and challenge virus was an unequivocal indicator of protective immunity. For example, while vaccination with either R-SHB18 or R-N2cT induced comparable VNA levels against CVS-N2c, the protective effect of R-SHB18 was 16-fold less than R-N2cT. Conversely, vaccination with R-SHBV18 protected 4-fold less against challenge with SHBRV-18 than vaccination with R-B2c333. These findings support the notion that there may be qualitative differences in protective capacity between different antibody populations, as seen with monoclonal antibodies. (Dietzschold, B., *Trends in Microbiology* 1:63–66, 1993).

Alternatively, there may be differences in the induction of cell mediated immune mechanisms.

The success of immunization of foxes in Europe with SAD-B19 indicates that natural reservoirs of rabies will be eliminated using live, non-neuroinvasive rabies viruses for vaccination. Using the above approaches, a recombinant rabies virus is engineered to express the ectodomain of any G that will induce a protective immune response in normal animals after peripheral infection, yet not invade the CNS and cause lethal disease. This will provide vaccines tailored for particular rabies virus reservoirs. Nevertheless, there are criteria other than G homology that determine the outcome of vaccination with a recombinant rabies virus. Until these are fully understood, empirical analysis of vaccine efficacy against a particular challenge virus must be performed. The potency of R-B2c333 against the different challenge viruses tested in the present invention indicates the potential of producing a vaccine that may be highly effective against the spectrum of enzootic rabies viruses and lead to eradication of natural rabies virus reservoirs in raccoons, skunks, and other animals.

The present invention relates to rabies viruses that cause greater cell death and are less pathogenic for the infected animal. This is because the rabies viruses of the present invention are more immunogenic. The gene encoding human cytochrome c is inserted into the rabies virus genome to accelerate the apoptotic process. This enhances the antiviral immune responses against the rabies virus, thereby attenuating the pathogenicity of the rabies virus. Expression of cytochrome c is markedly higher in cells infected with the recombinant virus carrying the active cytochrome c gene (SN-Cyto c (+)) than in cells infected with the recombinant virus containing the inactve cytochrome c gene (SN-Cyto c (−)). Furthermore, the level of apoptosis is strongly increased in primary neuron cultures infected with SN-Cyto c (+) as compared to neurons infected with SN-Cyto c (−). Because SN-Cyto c (+) and SN-Cyto c (−) have similar replication rates the increase in apoptosis seen in SN-Cyto c (+)-infected neurons is a direct consequence of cytochrome c over-expression as opposed to heightened expression of a potentially pro-apoptotic viral product such as G protein. This data confirm previous observations indicating that over-expression of cytochrome c results in an acceleration of apoptosis. (Bradham, C. A., et al., *Mol. Cell. Biol.* 18:6353–6364, 1998).

Morphological differences in the distribution of rabies N protein are also evident between cells infected with the two recombinant viruses. Analysis of rabies N protein expression by immunofluorescence reveals that while SN-Cyto c (−)-infected neurons show a constant fine granular staining pattern which extended into the neuronal processes, SN-Cyto c (+)-infected neurons show large N protein-positive inclusion bodies and almost no N protein staining in neuronal processes. The failure to translocate N protein to the periphery of SN-Cyto c (+)-infected neuronal cells is a result of the apoptotic process, which results in the depolymerization of actin filaments that are necessary for the intracellular transport of the N protein. (Ceccaldi, P. E., et al., *J. Gen. Virol.* 78:2831–2835, 1997; Morimoto, K., et al., *J. Virol.* 73:510–517, 1999).

As previously seen in the comparison of CVS-24 variants (Morimoto, K., et al., *J. Virol.* 73:510–517, 1999), the more cytopathic virus, SN-Cyto c (+), causes substantially less mortality following i.n. infection than SN-Cyto c (−), even though the latter is somewhat less pathogenic than the SPBN vector. Thus, a cause and effect relationship between the induction of apoptosis and the marked reduction in pathogenicity associated with SN-Cyto c (+) is revealed. Since the low mortality of SN-Cyto c (+) is paralleled by a strong reduction in the capacity to invade the CNS, the increased induction of apoptosis interferes with the progression of the infection into the CNS. Since the replication of SN-Cyto c (+) and SN-Cyto c (−) is comparable, there are two probable explanations for this observation: the infected neurons undergo apoptosis before the virus can spread to adjoining neurons, or the apoptosis drives a stronger, more rapid immune response that clears the virus before it spreads in the CNS.

After i.m. immunization, mice that receive SN-Cyto c (+) develop VNA titers that are, on average, three times higher than mice immunized with the same concentration of SN-Cyto c (−), regardless of the quantity of infectious virus particles used for immunization. The higher VNA titers in SN-Cyto c (+)-immunized mice confer greater protection against a lethal i.c. challenge infection with the highly pathogenic rabies virus strain CVS-N2c. Survivorship is significantly higher in the groups of mice immunized with SN-Cyto c (+) as compared to the groups of mice that receive SN-Cyto c (−), with the $ED_{50}$ of SN-Cyto c (+) being 20 times higher than that of SN-Cyto c (−). This clearly demonstrates that the immunogenicity of a live rabies vaccine virus is significantly enhanced, without modifying the production of viral proteins, by increasing its capacity to induce apoptosis. In the case of rabies virus, the protective immune response involves both G protein-specific VNA and cellular immune mechanisms. While other studies have largely focused on the effects of apoptosis on cellular aspects of immunity (Chattergoon M. A., et al., *Nature Biotechnology* 18:974–979, 2000; Rovere, P., et al., *J. Immunol.* 161–4467–4471, 1998; Shi, Y., et al., *Proc Natl. Acad. Sci.* 97:14590–14595, 2000), it is clear from the results disclosed herein that antibody responses are also enhanced by the apoptosis of infected cells.

The strong increase in immunogenicity coupled with the marked reduction in pathogenicity makes SN-Cyto c (+) a candidate for a live rabies virus vaccine. To be suitable for vaccination of wildlife, a rabies virus vaccine must be effective when given by the oral route. Comparison of VNA responses in mice orally immunized with SN-Cyto c (+), SN-10 (which is identical to SAD B19), and SN10-333 (which is similar to SAG1 or SAG2) clearly demonstrates that SN-Cyto c (+) is a superior oral vaccine to these extensively used standards. This has great significance for the development of new modified-live rabies vaccines for wildlife and stray dogs.

Rabies is a major zoonotic disease and remains an important public health concern causing approximately 60,000 annual deaths worldwide. (Martinez, L., *International J. Infect. Dis.* 4:222–228, 2000). In most developing countries, dogs represent the major reservoir of rabies virus. (Meslin, F. X., et al., In: *Lyssaviruses*, Rupprecht, C. E., et al., eds. Springer-Verlang, Berlin, Heidelberg, New York, 1–26, 1994). However, the situation in the Americas is much more complex, since large reservoirs of rabies viruses exist in many wild animal species (supra). (Rupprecht, C. E., et al., *Emerging Infectious Diseases* 1(4):107–114, 1995). Oral immunization of wildlife, with live vaccines such as the modified-live rabies virus vaccines SAD B19, SAG-1, and SAG-2 or the vaccinia-rabies glycoprotein recombinant virus vaccine VRG, is the most effective method to control and eventually eradicate rabies. (Wandeler, A. I., et al., *Rev. Infect. Dis.* 10 suppl. 4:649–653, 1988). Vaccination with modified-live rabies vaccines has resulted in almost complete eradication of vulpine rabies in Western Europe.

(Aubert, M. F. A., et al., In: *Lyssaviruses*, Rupprecht, C. E., et al., eds. Springer-Verlag, Berlin, Heidelberg, New York, 219–243, 1994; Blancou, J., & Meslin, F. X. In: *Laboratory techniques in rabies*, Meslin, F. X., et al., eds., World Health Organization, Geneva, Switzerland, 324–337, 1991; Wandeler, A. I., et al., *Rev. Infect. Dis.* 10 suppl. 4:649–653, 1988). On the other hand, while these vaccines induce protective immunity in foxes, neither SAD or ERA-based modified-live rabies vaccines nor recombinant vaccinia viruses work well in skunks (Rupprecht, C. E., et al., *J. Wildl. Dis.* 26:99–102, 1990; Wiktor, T. J., *Dev. Biol. Stand.*, 40:255–264, 1978; Wiktor, T. J., et al., *Proc. Natl. Acad. Sci.* 74:334–338, 1977; Wiktor, T. J., et al., *J. Ex. Med.* 145:1617–1622, 1977) or dogs. (Rupprecht, C. E., & Kieny, M. P., In: *Rabies*, Campbell, J. B., & Charlton, K. M. eds., Kluwe Academic, Boston, 335–364, 1988). In dogs, the administration of more than 109 infectious virus particles is required for minimum effect in the laboratory. (Rupprecht, C. E., & Kieny, M. P., In; *Rabies*, Campbell, J. B., & Charlton, K. M. eds., Kluwe Academic, Boston, 335–364, 1988). The widespread use of this amount of material is currently beyond feasible commercial production capacities. Furthermore, current modified-live rabies vaccines may actually cause disease. (Rupprecht, C. E. et al., *J. Wildl. Dis.* 26:99–102, 1990). Live rabies virus vaccine strains are modified using reverse genetics technology to express the pro-apoptotic protein cytochrome c. The resulting virus is unchanged antigenically but is considerably more immunogenic and spreads less readily to the CNS. These findings help explain why rabies viruses that strongly induce apoptosis of infected cells are less pathogenic to animals. The present invention provides for the development of safer and more potent wildlife rabies vaccines.

The present invention utilizes a glycoprotein from viruses with distinct neurotropisms to generate recombinant viruses that retain the tissue specificity of the parent virus. A further aspect of the present invention is to incorporate a pro-apoptotic gene (for example, cytochrome c) into a rabies virus to attenuate the pathogenicity and enhance the immunogenicity of the rabies virus. The present invention also relates to recombinant rabies viruses wherein the glycoprotein gene of a non-neuroinvasive rabies virus is replaced with a glycoprotein gene of a neuroinvasive rabies virus and this same virus vaccine has the pro-apoptotic protein engineered into the viral genome (supra). The rabies virus vaccines of the present invention do not affect the antigenic properties of the virus, allowing for an effective immune response against the rabies virus. By further incorporating a pro-apoptotic gene into the rabies virus vaccine apoptosis is induced in infected cells, allowing for an enhanced immune response against the rabies virus, and thus greater protection from any infecting rabies virus.

What is claimed is:

1. A vaccine comprising a non-neuroinvasive rabies virus wherein a glycoprotein gene of said non-neuroinvasive rabies virus is replaced with a glycoprotein gene of a neuroinvasive rabies virus to produce an attenuated recombinant rabies virus for vaccination.

2. The vaccine of claim 1 wherein said vaccination comprises an oral vaccination.

3. The vaccine of claim 1 wherein said attenuated recombinant rabies virus slows down an uptake of a rabies virus into a cell.

4. The vaccine of claim 3 wherein said cell is a neuron.

5. The vaccine of claim 1 wherein said glycoprotein gene of a neuroinvasive rabies virus comprises a glycoprotein gene encoding a cytoplasmic tail from a heterologous glycoprotein gene.

6. A vaccine comprising a rabies virus wherein a cytochrome c gene is inserted into said rabies virus such that cytochrome c is expressed from said cytochrome c gene to produce a recombinant rabies virus for vaccination.

7. The vaccine of claim 6 wherein said vaccination is an oral vaccination.

8. The vaccine of claim 6 wherein said cytochrome c induces an acceleration of apoptosis.

9. The vaccine of claim 8 wherein said acceleration of apoptosis enhances an immune response against said rabies virus.

10. The vaccine of claim 6 wherein said recombinant rabies virus vaccine attenuates the pathogenicity of a rabies virus.

11. A vaccine comprising a rabies virus wherein a cytochrome c gene is inserted into said rabies virus such that cytochrome c is expressed and further wherein a glycoprotein gene of said rabies virus is replaced with a glycoprotein gene of a neuroinvasive rabies virus to produce an attenuated recombinant rabies virus for vaccination.

12. The vaccine of claim 11 wherein said vaccination is an oral vaccination.

13. The vaccine of claim 11 wherein said glycoprotein gene of a neuroinvasive rabies virus comprises a glycoprotein gene encoding a cytoplasmic tail from a heterologous glycoprotein gene.

14. The vaccine of claim 11 wherein said glycoprotein gene of a neuroinvasive rabies virus comprises a change in an amino acid.

15. The vaccine of claim 11 wherein said cytochrome c induces an acceleration of apoptosis.

16. The vaccine of claim 15 wherein said acceleration of apoptosis enhances an immune response against said rabies virus.

* * * * *